(12) United States Patent
Lagudah et al.

(10) Patent No.: US 12,037,595 B2
(45) Date of Patent: *Jul. 16, 2024

(54) RUST RESISTANCE GENE

(71) Applicant: Commonwealth Scientific and Industrial Research Organisation, Acton (AU)

(72) Inventors: Evans Lagudah, Ngunnawal (AU); John Wallace Moore, Crestwood (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,137

(22) Filed: Jul. 14, 2022

(65) Prior Publication Data

US 2023/0203526 A1    Jun. 29, 2023

Related U.S. Application Data

(63) Continuation of application No. 16/840,017, filed on Apr. 3, 2020, now Pat. No. 11,421,246, which is a continuation of application No. 15/970,733, filed on May 3, 2018, now Pat. No. 10,647,992, which is a continuation of application No. 14/912,874, filed as application No. PCT/AU2014/000837 on Aug. 21, 2014, now Pat. No. 9,994,864.

(30) Foreign Application Priority Data

Aug. 21, 2013   (AU) .............................. 2013903161

(51) Int. Cl.
| | | |
|---|---|---|
| C12N 15/82 | (2006.01) | |
| A01N 65/08 | (2009.01) | |
| A01N 65/44 | (2009.01) | |
| C07K 14/415 | (2006.01) | |
| C12Q 1/54 | (2006.01) | |
| C12Q 1/6895 | (2018.01) | |
| G01N 33/50 | (2006.01) | |

(52) U.S. Cl.
CPC ......... *C12N 15/8282* (2013.01); *A01N 65/08* (2013.01); *A01N 65/44* (2013.01); *C07K 14/415* (2013.01); *C12Q 1/54* (2013.01); *C12Q 1/6895* (2013.01); *G01N 33/5035* (2013.01); *C12Q 2600/13* (2013.01); *C12Q 2600/158* (2013.01); *G01N 2333/415* (2013.01)

(58) Field of Classification Search
None
See application file for complete search history.

(56) References Cited

U.S. PATENT DOCUMENTS

| | | |
|---|---|---|
| 9,994,864 B2 | 6/2018 | Lagudah et al. |
| 10,557,147 B2 | 2/2020 | Lagudah et al. |
| 10,647,992 B2 | 5/2020 | Lagudah et al. |
| 11,421,246 B2 * | 8/2022 | Lagudah ................ A01N 65/44 |
| 2011/0223303 A1 | 9/2011 | Lagudah et al. |
| 2012/0216318 A1 | 8/2012 | La Rosa et al. |
| 2018/0327775 A1 | 11/2018 | Lagudah et al. |

FOREIGN PATENT DOCUMENTS

| | | |
|---|---|---|
| WO | WO 199641863 | 12/1996 |
| WO | WO 2000012736 | 3/2000 |
| WO | WO 2010022443 | 3/2010 |
| WO | WO 2020022443 | 1/2020 |
| WO | WO 2020/182515 | 9/2020 |
| WO | WO 2020/182515 A1 | 9/2020 |

OTHER PUBLICATIONS

BR122022017456-6 Written Opinion issued on Jan. 26, 2023 and its English translation (5 pages for OA) (8 pages of English translations).
BR1120160036719 Written Opinion issued on Oct. 4, 2022 and its English translation (5 pages for OA) (7 pages of English translations).
Bossolini, et al. "Development of simple sequence repeat markers specific for the Lr34 resistance region of wheat using sequence information from rice and Aegilops tauschii", Theor Appl Genet (2006) 113:1049-1062.
BR112016003671-9 Office Action dated May 10, 2022 pp. 1-5, English translation 6 pages.
Brueggeman, et al. "The barley stem rust-resistance gene Rpg1 is a novel disease-resistance gene with homology to receptor kinases", PNAS, vol. 99, No. 14, pp. 9328-9333, 2002.
Chinese Patent Application No. 201480052048.5, Second Office Action and its English translation dated Aug. 28, 2019, 8 pages.
Cloutier, et al. "Leaf rust resistance gene Lr1, isolated from bread wheat (*Triticum aestivum* L.) is a member of the large psr567 gene family", Plant Mol Biol (2007) 65:93-106.
Collins, et al. "Molecular Characterization of the Maize Rp1-D Rust Resistance Haplotype and its Mutants", The Plant Cell, vol. 11, 1365-1376, Jul. 1999.
Database Geneseq [Online] Aug. 21, 2008, "Protein useful for plant improvement. SEQ ID 15391" EBI accession No. GSP:ARP02344, 1 page.
Dyck, et al. "Genetics of Leaf Rust Reaction in Three Introductions of Common Wheat", Can. J. Genet. Cyhl. 19: 711-716, 1977.
Dyck, et al. "Inheritance of Adult-Plant Leaf Rust Resistance Derived from the Common Wheat Varieties Exchange and Frontana", Canadian Journal of Genetics and Cytology, 1966, vol. 8, No. 4: pp. 665-671.

(Continued)

*Primary Examiner* — Medina A Ibrahim
(74) *Attorney, Agent, or Firm* — Rudy J. Ng; Carol L. Francis; Bozicevic, Field & Francis LLP

(57) ABSTRACT

The present invention relates to new transporter polypeptides, and genes encoding therefor, which can be used to confer upon a plant resistance to one or more biotrophic fungal pathogens.

16 Claims, 13 Drawing Sheets

Figure 1:
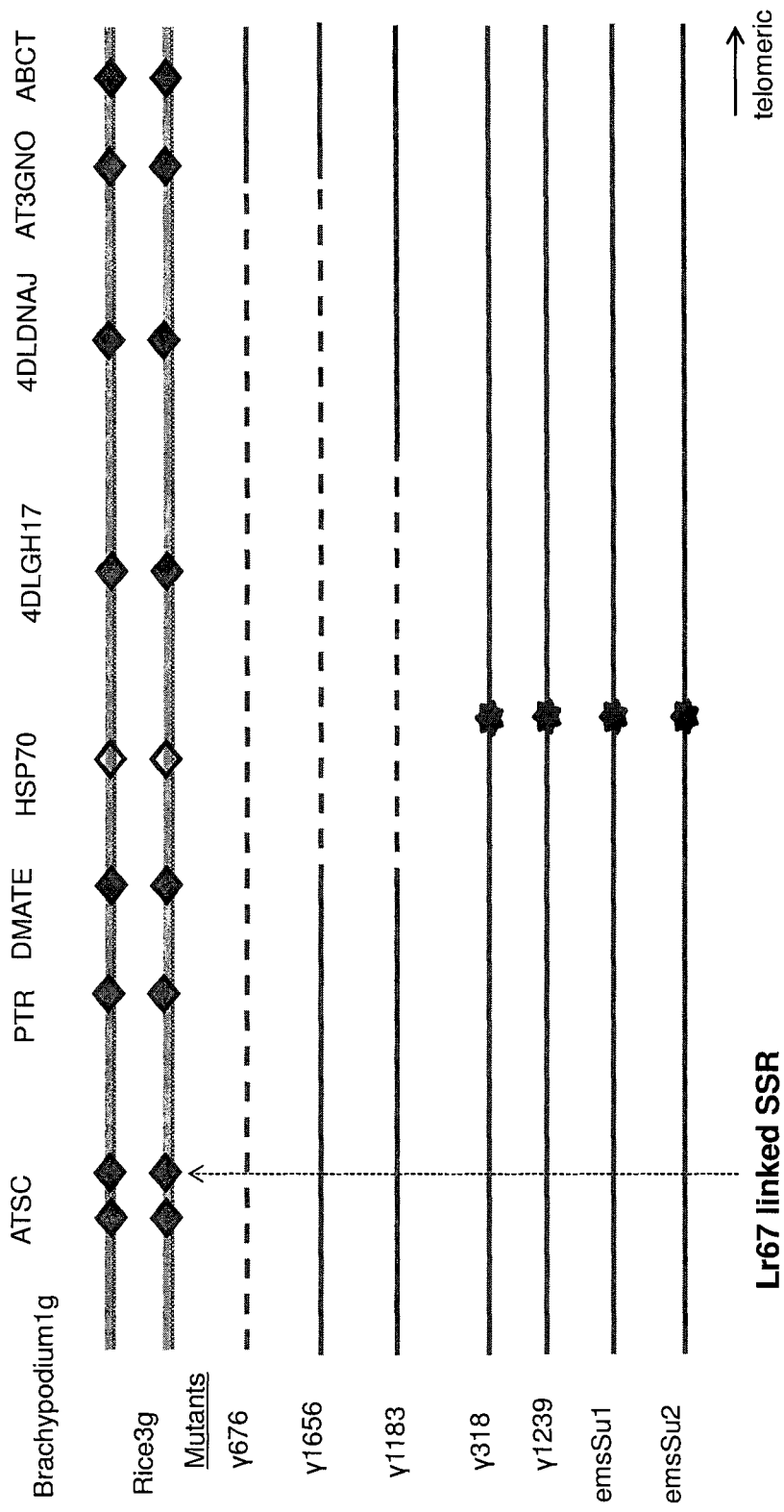

Specification includes a Sequence Listing.

(56) References Cited

OTHER PUBLICATIONS

Dyck, et al."An interchromosomal reciprocal translocation in wheat involving leaf rust resistance gene Lr34", Genome, vol. 37, 4 pages, 1994.
Dyck, et al."The association of a gene for leaf rust resistance with the chromosome 7D suppressor of stem rust resistance in common wheat", Genome vol. 29, 3 pages, 1987.
English translation of First Office Action for Chinese patent application 201480052048.5 dated Mar. 1, 2019.
English translation of Notification of Rejection Decision for Chinese Patent Application 201480052048.5 dated Aug. 3, 2020, 7 pages.
English translation of Office Action for Mexican Patent Application MX/a/2016/002214 dated Aug. 26, 2020.
EPO Communication for 14837281.6, dated Jan. 9, 2017.
EPO Extended European Search Report for 14837281.6, dated Dec. 21, 2016.
Examination report dated Oct. 2, 2020, Canada Application Serial No. 2921784, 1-8.
Examination Report dated Jul. 26, 2020, Indian Application Serial No. 20167007256, filed Mar. 2, 2013.
Feuillet et al., "Map-based isolation of the leaf rust disease resistance gene Lr10 from the hexaploid wheat (*Triticum aestivum* L.) genome", PNAS, vol. 100, No. 25, 15253-15258, 2003.
Gao et al., (2012) "Genetic analysis and molecular mapping of a new powdery mildew resistance gent Pm46 in common wheat", Theor Appl Genet, 125:967-973.
GenBank accession No. CAA47325.1, Mar. 13, 1997.
GenBank: AAQ24871.1, 1 page, Dec. 13, 2007.
GenBank accession No. AK099306, Dec. 4, 2008.
German, et al. "Effect of gene Lr34 in the enhancement of resistance to leaf rust of wheat", Theor Appl Genet (1992) 84:97-105.
Gupta et al., (2021) "The Medicago truncatula Sugar Transport Protein 13 and its Lr67res-Like Variant Confer Powdery Mildew Resistance in Legumes via Defense Modulation", Plant Cell Physiol. 62(4):650-667.
Herrera-Foessel et al. (2014) "Lr67 /Yr46 confers adult plant resistance to stem rust and powdery mildew in wheat" Theor. Appl. Genet. vol. 127, pp. 781-789.
Herrera-Foessel et al., (2011) "New slow-rusting leaf rust and stripe rust resistance genes Lr67 and Yr46 in wheat are pleiotropic or closely linked." Theoretical and Applied Genetics, 122: 239-249.
Hiebert et al., (2010) "An introgression on wheat Chromosome 4DL in RL6077 (Thatcher *6/PI 250413) confers adult plant resistance to stripe rust and leaf rust (Lr67)", Theor Appl Genet, 121:1083-1091.
Hruz and Mueckler (2001) "Structural analysis of the GLUT1 facilitative glucose transporter"; Mol Membr Biol. 18(3); pp. 183-193.
Huang, et al. "Map-Based Cloning of Leaf Rust Resistance Gene Lr21 from the Large and Polyploid Genome of Bread Wheat", Genetics 164: 655-664, 2003.
Jones (1999) "Protein Secondary Structure Prediction Based on Position-specific Scoring Matrices"; J Mol Biol. 292(2); pp. 195-202.
Joshi et al., "Leaf Tip Necrosis: A Phenotypic Marker Associated with Resistance to Spot Blotch Disease in Wheat", Crop Science Society of America, 44:792-796 (2004).
Kolmer et al., "Genetics of Resistance to Wheat Leaf Rust1", Annu. Rev. Phytopathol. 1996. 34:435-55.
Kolmer et al., (2003) "Physiologic Specialization of Puccinia triticina on Wheat in the United States in 2001", Plant Disease / vol. 87 No. 7, pp. 859-866.
Kolmer et al.,"Analysis of the Lr34/Yr18 Rust Resistance Region in Wheat Germplasm", Crop Science, vol. 48, Sep.-Oct. 2008, pp. 1841-1852.
Krattinger, et al. "A Putative ABC Transporter Confers Durable Resistance to Multiple Fungal Pathogens in Wheat", Science, vol. 323, 2009, pp. 1360-1363.

Lagudah et al., "Gene-specific markers for the wheat gene Lr34/ Yr18/Pm38 which confers resistance to multiple fungal pathogens", Theor Appl Genet (2009) 119:889-898.
Law et al., (2008) "Ins and outs of major facilitator superfamily antiporters"; Annu Rev Microbiol. 62; pp. 289-305.
Lemonnier et al., (2014) "'Expression of *Arabidopsis* sugar transport protein STP13 differentially affects glucose transport activity and basal resistance to Botrytis cinerea" Plant Mol. Bioi. vol. 85 pp. 473-484.
Liang et al., "Quantitative Trait Loci Mapping for Adult-Plant Resistance to Powdery Mildew in Bread Wheat", The American Phytopathological Society, vol. 96, No. 7, 2006, 784-789.
Lillemo et al., "The adult plant rust resistance loci Lr34/Yr18 and Lr46/Yr29 are important determinants of partial resistance to powdery mildew in bread wheat line Saar", Theor Appl Genet (2008) 116:1155-1166.
Manley et al., "Map Manager QTX, cross-platform software for genetic mapping", Mammalian Genome 12, 930-932 (2001).
McGuffin et al., (2000) "The PSIPRED protein structure prediction server"; Bioinformatics 16(4); pp. 404-405.
McIntosh, "2. History and status of the wheat rusts" Oral Papers 2009 Technical Workshop, pp. 11-23.
Moore et al., (2015) "A recently evolved hexose transporter variant confers resistance to multiple pathogens in wheat", Nature Genetics, 47(12):1494-1500.
NCBI Reference Sequence accession No. XM_004985118, Jun. 26, 2013.
Office Action issued for corresponding Mexican Patent Application No. MX/a/2016/002214, dated Feb. 19, 2021, 13 pages.
Pao et al., (1998) "Major Facilitator Superfamily"; Microbiol Mol Biol Rev. 62(1); pp. 1-34.
Ren et al., (2012) "QTL mapping of adult-plant resistance to stripe rust and leaf rust in Chinese wheat cultivar Bainong 64", Theor Appl Genet, 125:253-1262.
Response to first Examination report dated Oct. 28, 2020, Australia Application Serial No. 2014308558, 1-10.
Response filed to the examination report in relation to the corresponding Canadian Patent Application 2921784 filed on Jan. 29, 2021, pp. 1-29.
Response filed to the examination report in relation to the corresponding Indian Patent Application 201617007256 filed on Jan. 21, 2021, pp. 1-109.
Second Canadian Examination Report dated Oct. 6, 2021 regarding Canadian Patent Application No. 2,921,784, pp. 1-5.
Singh, "Association between Gene Lr34 for Leaf Rust Resistance and Leaf Tip Necrosis in Wheat", Crop Sci. 32:874-878 (1992).
Singh, "Genetic Association of Leaf Rust Resistance Gene Lr34 with Adult Plant Resistance to Stripe Rust in Bread Wheat", The American Phytopathological Society, vol. 82, No. 8, 1992, pp. 835-838.
Singh et al., "Genetics of adult plant resistance to stripe rust in ten spring bread wheats", Euphytica 72: 1-7,1994.
Skoppek et al., (2022) "The Barley HvSTP13GR Mutant Triggers Resistance against Biotrophic Fungi", Mol Plant Pathol. 23(2):278-290.
Sonnhammer et al., (1998) "A hidden Markov model for predicting transmembrane helices in protein sequences"; Proc Int Conf Intell Syst Mol Biol. 6; pp. 175-182.
Spielmeyer et al., (2013) "Lr67 and Lr34 rust resistance genes have much in common—they confer broad spectrum resistance to multiple pathogens in wheat", BMC Plant Biology, 13(96):10 pages.
Spielmeyer et al., "Fine scale genetic and physical mapping using interstitial deletion mutants of Lr34/Yr18: a disease resistance locus eVective against multiple pathogens in wheat", Theor Appl Genet (2008) 116:481-490.
Spielmeyer, et al. "Powdery Mildew resistance and Lr34/Yr18 genes for durable resistance to leaf and stripe rust cosegregate at a locus on the short", Theor Appl Genet (2005) 111:731-735.
Summons to attend oral proceedings which issued in relation to corresponding European patent application 14837281.6, dated Jul. 2, 2019.
Sun et al (2012) "Crystal structure of a bacterial homologue of glucose transporters GLUT1-4", Nature 490, pp. 361-366.

(56) References Cited

OTHER PUBLICATIONS

Sun et al (2012) "Functionally important amino acids in rice sucrose transporter OsSUT1", Biochemistry. 51(15); pp. 3284-3291.
Truernit et al. (1996) "The Sink-Specific and Stress-Regulated *Arabidopsis* STP4 Gene: Enhanced Expression of a Gene Encoding a Monosaccharide Transporter by Wounding, Elicitors, and Pathogen Challenge", The Plant Cell, 8:2169-2182.
UniProtKB accession No. R7WC49, Jul. 24, 2013.
UniProtKB accession No. W5ELX6, Mar. 19, 2014.
Whisstock & Lesk (2003) "Prediction of protein function from protein sequence and structure", Quarterly Reviews of Biophysics. 36(3):307-340.
Written Opinion dated Aug. 8, 2023 and its English translation which issued in relation to corresponding Brazilian Patent Application 1220220174566 (Divisional of BR BR1120160036719), 4 pages.
Gupta et al., "The *Medicago truncatula* Sugar Transport Protein 13 and is Lr67res-Like Variant Confer Powdery Mildew Resistance in Legumes via Defense Modulation" Plant & Cell Physiology (2021) 62(4):650-667.
Law et al., "Ins and Outs of Major Facilitator Superfamily Antiporters" Annu Rev Microbiol (2008) 62:289-305.
R. Lemoine., "Sucros transporters in plants: update on function and structure" Biochimica et Biophysica Acta (2000) 1465:246-262.
Pao et al., "Major Facilitator Superfamily" Microbiology and Molecular Biology (Mar. 1998) 62(1):1-34.
Skoppek et al., "The barley HvSTP13GR mutant triggers resistance against biotrophic fungi" Molecular Plant Pathology (2022) 23:278-290.

* cited by examiner

MPGGGFAVSAPSGVEFEAKITPIVIISCIMAATGGLMFGYDVGISGGVTSMDDFLREFFPAVLRRKNQDKESNYC
KYDNQGLQLFTSSLYLAGLTATFFASYTTRRLGRRLTMLIAGVFFIIGVIFNGAAQNLAMLIIGRILLRCGVGFA
NQAVPLFLSEIAPTRIRGGLNILFQLNVTIGILFANLVNYGTSKIHPWGWRLSLSLAGIPAAMLTLGALFVTDTP
NSLIERGHLEEGKAVLKRIRGTDNVEPEFNEIVEASRIAQEVKHPFRNLLQRRNRPQLVIAVLLQIFQQFTGINA
IMFYAPVLFNTLGFKSDASLYSAVITGAVNVLATLVSVYAVDRAGRRALLLEAGVQMFLSQVVIAVVLGIKVTDK
SDNLGHGWAILIVVMVCTYVASFAWSWGPLGWLIPSETFPLETRSAGQSVTVCVNLLFTFLIAQAFLSMLCHLKF
AIFIFFSAWVLVMSVFVLFFLPETKNVPIEEMTDKVWKQHWFWKRFMDDDDHHHNIANGKNATV

Figure 5

TCCTCGTGTGCTTCTGTGGAGAAACACTCGCTGCTTGTCTAGCTTCCATTATATCGGCGTAGCTTGACCGGCCGG
CTTGCGAAGATGCCGGGCGGGGGGTTCGCCGTGTCGGCGCCGTCCGGCGTGGAGTTCGAGGCCAAGATCACGCCC
ATCGTCATCATCTCCTGCATCATGGCGGCCACCGGCGGCCTCATGTTCGGCTACGACGTCGGCATCTCAGGCGGA
GTGACATCGATGGACGATTTCCTGCGTGAGTTCTTCCCGGCGGTGCTGCGCCGGAAGAACCAGGACAAGGAGAGC
AACTACTGCAAGTACGACAACCAGGGCCTGCAGCTCTTCACCTCGTCGCTCTACCTCGCCGGCCTCACCGCCACC
TTCTTCGCCTCCTACACCACCCGCCGCCTCGGACGCCGCCTCACCATGCTCATCGCCGGCGTCTTCTTCATCATC
GGCGTCATCTTCAACGGGGCCGCCCAGAACCTCGCCATGCTCATCATCGGCAGGATCCTGCTTCGTTGCGGCGTC
GGCTTCGCCAACCAGGCCGTTCCCCTGTTCCTGTCGGAGATCGCGCCGACGAGGATCCGCGGCGGGCTCAACATC
CTGTTCCAGCTGAACGTGACCATCGGCATCCTGTTCGCGAACCTGGTGAACTACGGCACGAGCAAGATCCACCCG
TGGGGCTGGCGGCTGTCGCTGTCGCTGGCCGGCATCCCGGCGGCGATGCTCACCCTGGGCGCGCTCTTCGTCACC
GACACCCCCAACAGCCTCATCGAGCGCGGCCACCTGGAGGAGGGCAAGGCGGTGCTCAAGCGGATCCGCGGCACC
GACAACGTGGAGCCGGAGTTCAACGAGATCGTGGAGGCGAGCCGCATCGCGCAGGAGGTGAAGCACCCGTTCCGG
AACCTGCTCCAGCGCCGGAACCGCCCGCAGCTGGTCATCGCCGTGCTGCTCCAGATCTTCCAGCAGTTCACGGGG
ATCAACGCCATCATGTTCTACGCCCCCGTGCTGTTCAACACGCTCGGGTTCAAGAGCGACGCGTCGCTCTACTCG
GCGGTGATCACGGGCGCCGTCAACGTGCTGGCCACGCTGGTGTCGGTGTACGCCGTGGACCGCGCCGGGCGGCGC
GCGCTGCTGCTGGAGGCTGGCGTGCAGATGTTCCTGTCGCAGGTGGTGATCGCCGTGGTGCTGGGCATCAAGGTG
ACGGACAAGTCGGACAACCTGGGCCACGGGTGGGCCATCCTGTGGTGGTCATGGTGTGCACCTACGTGGCCTCC
TTCGCCTGGTCCTGGGGCCCGCTGGGGTGGCTCATCCCAGCGAGACGTTCCCGCTGGAGACGCGGTCGGCGGGG
CAGAGCGTGACGGTGTGCGTCAACCTGCTCTTCACCTTCCTCATCGCGCAGGCCTTCCTCTCCATGCTCTGCCAC
CTCAAGTTCGCCATCTTCATCTTCTTCTCGGCCTGGGTGCTCGTCATGTCCGTCTTCGTGCTCTTCTTCCTCCCG
GAGACCAAGAACGTGCCCATCGAGGAGATGACCGACAAGGTGTGGAAGCAGCACTGGTTCTGGAAGAGATTCATG
GACGACGACGACCACCACCACAACATCGCCAACGGCAAGAACGCCACCGTCTGAAAGTTGCTCCTACTATGT

Figure 6

MPGGGFAVSAPSGVEFEAKITPIVIISCIMAATGGLMFGYDVGISGGVTSMDDFLREFFPAVLRRKNQDKESNYC
KYDNQGLQLFTSSLYLAGLTATFFASYTTRRLGRRLTMLIAGVFFIIGVIFNGAAQNLAMLIIGRILLSCGVGFA
NQAVPLFLSEIAPTRIRGGLNILFQLNVTIGILFANLVNYGTSKIHPWGWRLSLSLAGIPAAMLTLGALFVTDTP
NSLIERGHLEEGKAVLKRIRGTDNVEPEFNEIVEASRIAQEVKHPFRNLLQRRNRPQLVIAVLLQIFQQFTGINA
IMFYAPVLFNTLGFKSDASLYSAVITGAVNVLATLVSVYAVDRAGRRALLLEAGVQMFLSQVVIAVVLGIKVTDK
SDNLGHGWAILVVVMVCTYVASFAWSWGPLGWLIPSETFPLETRSAGQSVTVCVNLLFTFLIAQAFLSMLCHLKF
AIFIFFSAWVLVMSVFVLFFLPETKNVPIEEMTDKVWKQHWFWKRFMDDDDHHHNIANGKNATV

Figure 7

```
TCCTCGTGTGCTTCTGTGGAGAAACACTCGCTGCTTGTCTAGCTTCCATTATATCGGCGTAGCTTGACCGGCCGG
CTTGCGAAGATGCCGGGCGGGGGGTTCGCCGTGTCGGCGCCGTCCGGCGTGGAGTTCGAGGCCAAGATCACGCCC
ATCGTCATCATCTCCTGCATCATGGCGGCCACCGGCGGCCTCATGTTCGGCTACGACGTCGGCATCTCAGGCGGA
GTGACATCGATGGACGATTTCCTGCGTGAGTTCTTCCCGGCGGTGCTGCGCCGGAAGAACCAGGACAAGGAGAGC
AACTACTGCAAGTACGACAACCAGGGCCTGCAGCTCTTCACCTCGTCGCTCTACCTCGCCGGCCTCACCGCCACC
TTCTTCGCCTCCTACACCACCCGCCGCCTCGGACGCCGCCTCACCATGCTCATCGCCGGCGTCTTCTTCATCATC
GGCGTCATCTTCAACGGGGCCGCCCAGAACCTCGCCATGCTCATCATCGGCAGGATCCTGCTTGGTTGCGGCGTC
GGCTTCGCCAACCAGGCCGTTCCCCTGTTCCTGTCGGAGATCGCGCCGACGAGGATCCGCGGCGGGCTCAACATC
CTGTTCCAGCTGAACGTGACCATCGGCATCCTGTTCGCGAACCTGGTGAACTACGGCACGAGCAAGATCCACCCG
TGGGGCTGGCGGCTGTCGCTGTCGCTGGCCGGCATCCCGGCGGCGATGCTCACCCTGGGCGCGCTCTTCGTCACC
GACACCCCCAACAGCCTCATCGAGCGCGGCCACCTGGAGGAGGGCAAGGCGGTGCTCAAGCGGATCCGCGGCACC
GACAACGTGGAGCCGGAGTTCAACGAGATCGTGGAGGCGAGCCGCATCGCGCAGGAGGTGAAGCACCCGTTCCGG
AACCTGCTCCAGCGCCGGAACCGCCCGCAGCTGGTCATCGCCGTGCTGCTCCAGATCTTCAGCAGTTCACGGGG
ATCAACGCCATCATGTTCTACGCCCCCGTGCTGTTCAACACGCTCGGGTTCAAGAGCGACGCGTCGCTCTACTCG
GCGGTGATCACGGGCGCCGTCAACGTGCTGGCCACGCTGGTGTCGGTGTACGCCGTGGACCGCGCCGGGCGGCGC
GCGCTGCTGCTGGAGGCTGGCGTGCAGATGTTCCTGTCGCAGGTGGTGATCGCCGTGGTGCTGGGCATCAAGGTG
ACGGACAAGTCGGACAACCTGGGCCACGGGTGGGCCATCCTGGTGGTGGTCATGGTGTGCACCTACGTGGCCTCC
TTCGCCTGGTCCTGGGGCCCGCTGGGGTGGCTCATCCCCAGCGAGACGTTCCCGCTGGAGACGCGGTCGGCGGGG
CAGAGCGTGACGGTGTGCGTCAACCTGCTCTTCACCTTCCTCATCGCGCAGGCCTTCCTCTCCATGCTCTGCCAC
CTCAAGTTCGCCATCTTCATCTTCTTCTCGGCCTGGGTGCTCGTCATGTCCGTCTTCGTGCTCTTCTTCCTCCCG
GAGACCAAGAACGTGCCCATCGAGGAGATGACCGACAAGGTGTGGAAGCAGCACTGGTTCTGGAAGAGATTCATG
GACGACGACGACCACCACCACAACATCGCCAACGGCAAGAACGCCACCGTCTGAAAGTGTTGCTCCTACTATGT
```

Figure 8

```
Lr67(res)    1    MPGGGFAVSAPSGVEFEAKITPIVIISCIMAATGGLMFGYDVGISGGVTSMDDFLREFFP    60
                  * ****** ** +***************************+****   *** +****
Arath        1    MTGGGFATSA-NGVEFEAKITPIVIISCIMAATGGLMFGYDVGVSGGVTSMPDFLEKFFP    59

Lr67(res)    61   AVLRR--KNQDKESNYCKYDNQGLQLFTSSLYLAGLTATFFASYTTRRLGRRLTMLIAGV   118
                  *****    **+************************************************
Arath        60   VVYRKVVAGADKDSNYCKYDNQGLQLFTSSLYLAGLTATFFASYTTRTLGRRLTMLIAGV   119

Lr67(res)    119  FFIIGVIFNGAAQNLAMLIIGRILLRCGVGFANQAVPLFLSEIAPTRIRGGLNILFQLNV   178
                  ****** * ***+* ******* *****************************
Arath        120  FFIIGVALNAGAQDLAMLIAGRILLGCGVGFANQAVPLFLSEIAPTRIRGGLNILFQLNV   179

Lr67(res)    179  TIGILFANLVNYGTSKIHP-WGWRLSLSLAGIPAAMLTLGALFVTDTPNSLIERGHLEEG   237
                  **************** +*** + **** *+*+**** +****
Arath        180  TIGILFANLVNYGTAKIKGGWGWRLSLGLAGIPALLLTVGALLVTETPNSLVERGRLDEG   239

Lr67(res)    238  KAVLKRIRGTDNVEPEFNEIVEASRIAQEVKHPFRNLLQRRNRPQLVIAVLLQIFQQFTG   297
                  ***+*********** +++**** *+***+*******************  ** **
Arath        240  KAVLRRIRGTDNVEPEFADLLEASRLAKEVKHPFRNLLQRRNRPQLVIAVALQIFQQCTG   299

Lr67(res)    298  INAIMFYAPVLFNTLGFKSDASLYSAVITGAVNVLATLVSVYAVDRAGRRALLLEAGVQM   357
                  ********** ***** ****+++****+ **********  +*+**+  **********
Arath        300  INAIMFYAPVLFSTLGFGSDASLYSAVVTGAVNVLSTLVSIYSVSVDKVGRRVLLEAGVQM   359
```

Figure 9

```
Lr67(res)   358  FLSQVVIAVVLGIKVTDKSDNLGHGWAILLVVMVCTYVASFAWSWGPLGWLIPSETFPLE  417
                 * ******++****  * **   *+***+*****+************************
Arath       360  FFSQVVIAIILGVKVTDTSTNLSKGFAILVVVMICTYVAAFAWSWGPLGWLIPSETFPLE  419

Lr67(res)   418  TRSAGQSVTVCVNLLFTFLIAQAFLSMLCHLKFAIFIFFSAWVLVMSVFVLFFLPETKNV  477
                 ************************** *** ************+* ********* +
Arath       420  TRSAGQSVTVCVNLLFTFIIAQAFLSMLCHFKFGIFIFFSAWVLIMSVFVMFLLPETKNI  479

Lr67(res)   478  PIEEMTDKVWKQHWFWKRFMDDDDHHHNI----ANGKNATV                    514
                 ******+**+*** ****** ***   +    +****
Arath       480  PIEEMTERVWKKHWFWARFMDDHNDHEFVNGEKSNGKSNGFDPSTRL              526
```

Figure 9 (continued)

```
Lr67(res)    1   MPGGGFAVSAPSGVEFFEAKITPIVIISCIMAATGGLMFGYDVGISGGVTSMDDFLREFFP    60
                 * ****+**    ***************************************++******
Oryza        1   MA-GGFSVSG-SGVEFFEAKITPIVIISCIMAATGGLMFGYDVGISGGVTSMDDFLREFFP    58

Lr67(res)   61   AVLRRKNQDKESNYCKYDNQGLQLFTSSLYLAGLTATFFASYTTRRLGRRLTMLIAGVFF   120
                 ++*+**************************************************+****
Oryza       59   TVLKKHEDKESNYCKYDNQGLQLFTSSLYLAGLTATFFASYTTRRLGRRLTMLIAGVFF   118

Lr67(res)  121   IIGVIFNGAAQNLAMLIIGRILLRCGVGFANQAVPLFLSEIAPTRIRGGLNILFQLNVTI   180
                 *+************+******+********************************
Oryza      119   IVGVIFNGAAQNLAMLIVGRILLGCVGFANQAVPLFLSEIAPTRIRGGLNILFQLNVTI   178

Lr67(res)  181   GILFANLVNYGTSKIHPWGWRLSLSLAGIPAAMLTGALFVTDTPNSLIERGHLEEGKAV   240
                 *****************+*****************+*************+******
Oryza      179   GILFANLVNYGTAKIHPWGWRLSLSLAGIPAALLTGALFVVDTPNSLIERGRLEEGKAV   238

Lr67(res)  241   LKRIRGTDNVEPEFNEIVEASRIAQEVKHPFRNLLQRRNRPQLVIAVLLQIFQQFTGINA   300
                 *+++***********************+*******************************
Oryza      239   LRKIRGTDNVEPEFNEIVEASRVAQEVKHPFRNLLQRRNRPQLVIAVLLQIFQQFTGINA   298

Lr67(res)  301   IMFYAPVLFNTLGFKSDASLYSAVITGAVNVLATLVSVYAVDRAGRRALLLEAGVQMFLS   360
                 ************+************+*   ***   *+***     **** ********
Oryza      299   IMFYAPVLFNTLGFKTDASLYSAVITGAVNVLSTLVSVSADRVGRRMLLLEAGVQMFLS   358
```

Figure 10

```
Lr67(res)  361  QVVIAVVLGIKVTDKSDNLGHGWAILLVVMVCTYVASFAWSWGPLGWLIPSETFPLETRS  420
                 ** ************+*************+*****************************
Orysa      359  QVAIAVVLGIKVTDRSDNLGHGWAIMVVVMVCTFVSSFAWSWGPLGWLIPSETFPLETRS  418

Lr67(res)  421  AGQSVTVCVNLLFTFLIAQAFLSMLCHLKFAIFIFFSAWVLVMSVFVLFFLPETKNVPIE  480
                ****************************+****  ********+**********+****
Orysa      419  AGQSVTVCVNLLFTFVIAQAFLSMLCHLKYAIFAFFSAWVVVMSLFVLFFLPETKNIPIE  478

Lr67(res)  481  EMTDKVWKQHWFWKRFMDDDDHHHNIANG-KN--ATV  514
                ****+************** * *** + ** *+  ***
Orysa      479  EMTERVWKQHWFWKRFMDDADKHHVVPNGGKSNGATV  515
```

Figure 10 (continued)

ATGGCGGCCGGCGGTTCCGCCGTCTCGCCGCCGTCCGGGGTGGAGTTCGAGGCCAAGATCACCGCCATCGTCATCATC
TCCTGCATCATGGCGGCCACCGGCGGCGTCATCTTCGGCTACGACGTCGCCATCTCACGTAACCCGATACTCCACATG
TCTATGCAAGTTCTTCCAGAGATCGATCATCTCCGTCCATGCATGTGCGTGCGTTGCGTGCTCCCGTGGTAGCTCTGA
GAAATCATGTCAAATCCGCCTTACATGCATGGTTTAGTGATCCGTGACGTCGCCGTCCGCGCGTATGAAAGAGAGGAG
TTTAATTGACTCCATGGATATGGATATGGTGTTTACTTGTGGCTGCCGTCTCTCGTCTTCATATGACGAAGCAGATAA
CCACAGATAATTGGAAGGAAGTTAATGCAATTGATCCTCCTCATTAACTACCACGCACCGGCCAGCTGATAATTTAGC
ACTTTCCAGTTTACTCCATTGTGAACACTATCCGGTTTTCTGGCCAGGATCATAGTATATGCTCGCACTTGTGCTAGC
TGTATGATTCTAGCTGCATATAAGAATTAATATTATACTGTATTTGGAAGAAACTATATAACTGCTGCCATCTTGCCA
CCGACTACTTTGACAGGCTGTTAAGTCAACCCATTTGTACACCTCCAGATCACGTCTGATGCAACAAAGCTGTCTTTT
GTGTGGACACGTTGCCTTTGGGTTTAGCATAGTATTACATGAATTCTTACTAAACTTTTTTTGCGAGATGAATTCTT
ACTAAAACTAATTAAGAAAATCTTGTCCATTTCTTTCACAGCGTCCAGCTCGATTAACAACCAGTTCTAAGGTCTAAA
AACTGTTTGTTTTTGCAGGCGGACTGACATCGATGGAGGATTTCCTCCGTGACTTCTTCCGGCGCGTGCTGCGCCGGA
AGAAGCAGCACAAGCAGAGCGAACTACATGCAAGTACGACAACGAGGGCGTGCAGCTCTTCACCTCGTGGCTCACGTC
CCGGCGGTCACCGCAGCTTGTTGGCCTCCTACAGCTACCCGGCGGCTCGGACGCGGCTCACCATGGTCATGGCCGGCC
GCTTGTTCATCGGCGTCATCTTGAACGGGGCGCCCAGAACCTCGCCATGCTCATCATCGCCAGGATGGTCGTTT
GTTGCGGCGTTCGGCAACCAGGTTAGCACAAATTTCCACCAGCTTCAGAATTGTATATTTTTTAATATCAGTA
AGCAAGATTACGTACGTTTACGCAGCAACATTTGATATGTACGTACTCCTAGGTAACTTAAGTCAAAGGTGTTGGTA
GAAACCGAAGTCAAACATGTAAAGCTAGCGGTGGCTGGTTGAGAAAATATGTACGTAGCACGCACACGCACGAGACA
TAATTTTCCGCGTCTACGAAAATGACGTAACCCGTGTGCAGTTTCTTCCTTGTTTGCTGGCAATCAGTCACCGCCCAC
GGTAGTATCAAAGAATCTTTGGACCAAACTAAACCTACTGGTCCTACCATTTTTCACGTCCAGATTAATACTCTTCTA
AATATAAAATATTGTTGTATTTTATACTCCCTCCGTTCCTAAATATAAATCTTTTTAGACATTTCAAATGAACTACAA
CATACGGATGTATGTAGGCATATTTAGAGTGTAGATTCACTCATTTTGCTCCGTATTCGGTCACTTGTTGGAAAGAC
TTATATTTGGGAACGGAGGGAGTATGTACTAGCTGCAGTACGTATGTAGGTACATCGTATCCCTCTTATATTTCCCGG
AATTCAGGGGTCAAATGTACAAACCATGTGACGGTGCATGACTCGTGTTGGCGCACGAGGACACCTTCCATTGGTGGC
ATCGCCTCACCTCTCGCGATAAACTTGTTAAGTTCCAAGATTCCGATGCTGGCCGCGACCCCGAGCTTAGAAATTACT
GGACCAAATGGTAGGAGAAGCTTGGGCCAAGCAACAGGTGATAGGTGCACGCTTGCAGCTTATCCCCTTGGTTTCTCA
TGGTTTTACTAGTCTCTGCAGCAGCAGAGTTTGCTGGTGTGGCTGCCCTTCTCTCGTTGTCCCAAGTTGCAATCAA
CTTGGACTAGTTGTAGAATATACAAACACAGCAGCTTTGGATTCTTCTGTTTTTGGCTGTCGAAACTTTGATTTTAAT
AGCGAAATTGCTTCACGGACGATACTTTCCGCACGATCCGTGAACGATTCTTCCTTCGCGTCCAAATCTCATGCTTGC
ACGCACGCTGTGGCGCTGTCATGTAGGATCGTTCAGGCCTCGACGCAAATCTATCGTGTGTGTAGCAACACTTTTTA
GTAGTAGCAAGCAGGCGCGGTTGTTCACGTGTAGGCCACACGGGTCGCAATATGAAGCGAGCCTAGCTGATAGAGTAG
TTATACATAAACTTAGGCCTGGACCAAAATTGTATCTTTGATGCTTGACTTGGAGGTGCACTTCGCTTGGATTCTTCT
GGTTCCTTCCTTGCCGAACACCGGAAAAAAAACAATGTGTCTATGGACTGTAGACCTCAGAGCGGGGAGCTTTCTCG
ATTGAAAATGCCAAGAATTTGTGCGCTAGTGATGCATTAGATTACTACACGGATCAAGGCACTGATTGAGCATGAGTT
TGCAAATTATGCACACACTAACATCCAAAAAAAAAAACCAAACGTACTTGTATAATATAAAGGCGTCTAGACTCAATT
ATACTCCGTACGAAGCAGGCAAGACAACATGCATGTGTGCCAGAACTTAGCTCGAGTAGGAGTAGATCATTAGTCCAA
CAATATTTTATTACTTAATTCCACCGCTTCTGATTAGGCCCACTGATTAAGAGATTCCGATGGTGATAGGTTGGTGCG
GTTCTGACACTTTAATTATACGGTCACATGCTAAGGTGATTTTTTTTACAGTAGGAAAGCATGCTAGGTGATTTGT
TTTAGCATCCCAAGAAAAGGAAAGAAAAAAGGGGAAGAGAACATTCTGGCCCAATGGGCCTCGTTCAGGCCATCTGCA
TTTTTTTTTTGCGGGGACAGGCCATCTGCATTTGATGACCCATTTCGTGATTTCCCGTCTCAGAATTTCTTCTTACTA
TACATTTCTAACGAAACGAACAACTGTGGTGCAGCCCGTTCCGTCTGTCGGAGATCGCGGCGGACGAGGATCCG
CGGCGGCGTCAACATCCTGTTGCAGCTGAAGGTGACGATGGCATCCTGTTCCGGCGAACCTGCTGAACTACGGCACCAG
CAAGATCGACCGTGCGGCTCCGCGTGTCGGCGGCGGCATCCGGCGGCGATGCTGACAGCTGAAGTACGGCATCGGCGCT
CTTCGTGACCGACAACGCCCAACAGCCTCATCGAGCGGGCCACCTGCAGGAGGCAGCGGCGTCGACGCAAGCACCCGT
CCGCACCGACAACGTCGACCGGACGTTCAACACAGCATCGTGGAGGCCAGCGGCATCGCGAGGAGCTGAAGCACCCGT
CCGGAAGCTGCTCCAGCGCCGGAACGGCCCGCAGCTCGTCATGCCCGTGCTGCTCGAGATTGCAGCACTTCAGGGC
GATCAACGCCATCATGTTCTACCGCGCCGTGCTGTTCAACACGCTCGGCGTTCAAGAGCGACGCGCTCGCTACTGGCG
GGTCATCACGGCGCCGTCAACGTGCTGCCACGCTGCCTCGGCGTGTACCCCGTCGACCGCCGGGGCGGCGGCCGGCC
GCTGCTGGAGGCTGCCGTGCAGATGTTCCTGTGCGAGCGCCGTCGATCGCCGTGGTGCTGCCATCAAGGTCACGCAAA
GTCGAGAACGCTGGCCACGGTGGGCCATCGTGGCTGCTCATGGTGTGCACGTGCAGCAGTTCGCCGGCGCTGGT
CTGGGGCGCTGGGCGGCCATGGCCCAGCCAGACGTCGCCGTGAACGCGGCCGGCGGCAGCGGTCACGGT
GTCGTCAACGTCGCTTCACGGTTCCTCATCGGCGACGGCCGGACTTCCATGCTCTGCCACCTCAAGTTCGCCATCTT
CATCTTCTTCGGCCTCTGGCCTCCTCAGTCGTCGTCGCGTCTCTTCCTCCGGACGCAACAACGTGCCAT
CGAGGAGATGACCGACAAGGTCGTGAAGCAGCAGCTGCTTCTGGAAGACATTCATGGACGACGAGGACGACCACCACAA
CATCGCCAACGCCGAAGAACGGCACCGTCTCTGA

Figure 14

SEQUENCE LISTING

```
Sequence total quantity: 10
SEQ ID NO: 1           moltype = AA  length = 514
FEATURE                Location/Qualifiers
source                 1..514
                       mol_type = protein
                       organism = Triticum aestivum
SEQUENCE: 1
MPGGGFAVSA PSGVEFEAKI TPIVIISCIM AATGGLMFGY DVGISGGVTS MDDFLREFFP  60
AVLRRKNQDK ESNYCKYDNQ GLQLFTSSLY LAGLTATFFA SYTTRRLGRR LTMLIAGVFF  120
IIGVIFNGAA QNLAMLIIGR ILLRCGVGFA NQAVPLFLSE IAPTRIRGGL NILFQLNVTI  180
GILFANLVNY GTSKIHPWGW RLSLSLAGIP AAMLTLGALF VTDTPNSLIE RGHLEEGKAV  240
LKRIRGTDNV EPEFNEIVEA SRIAQEVKHP FRNLLQRRNR PQLVIAVLLQ IFQQFTGINA  300
IMFYAPVLFN TLGFKSDASL YSAVITGAVN VLATLVSVYA VDRAGRRALL LEAGVQMFLS  360
QVVIAVVLGI KVTDKSDNLG HGWAILLVVM VCTYVASFAW SWGPLGWLIP SETFPLETRS  420
AGQSVTVCVN LLFTFLIAQA FLSMLCHLKF AIFIFFSAWV LVMSVFVLFF LPETKNVPIE  480
EMTDKVWKQH WFWKRFMDDD DHHHNIANGK NATV                              514

SEQ ID NO: 2           moltype = DNA  length = 1545
FEATURE                Location/Qualifiers
source                 1..1545
                       mol_type = other DNA
                       organism = Triticum aestivum
SEQUENCE: 2
atgccgggcg gggggttcgc cgtgtcggcg ccgtccggcg tggagttcga ggccaagatc  60
acgcccatcg tcatcatctc ctgcatcatg gcggccaccg gcggcctcat gttcggctac  120
gacgtcggca tctcaggcgg aagtgacatc gatggacgatt tcctgcgtga gttcttccgg  180
gcggtgctgc gccggaagaa ccaggacaag gagagcaact actgcaagta cgacaaccag  240
ggcctgcagc tcttcacctc gtcgctctac ctcgccggcc tcaccgccac cttcttcgcc  300
tcctacacca cccgccgcct cggacgccgc ctcaccatgc tcatcgccgg cgtcttcttc  360
atcatcgcg tcatcttcaa cggggccgcc cagaacctcg ccatgctcat catcggcagg  420
atcctgcttc gttgcgcgt cggcttcgcc aaccaggccg ttccccgtt cctgtcgag  480
```

-continued

```
atcgcgccga cgaggatccg cggcgggctc aacatcctgt tccagctgaa cgtgaccatc    540
ggcatcctgt tcgcgaacct ggtgaactac ggcacgagca agatccaccc gtggggctgg    600
cggctgtcgc tgtcgctggc cggcatcccg gcggcgatgc tcaccctggg cgcgctcttc    660
gtcaccgaca cccccaacag cctcatcgag cgcggccacc tggaggaggg caaggcggtg    720
ctcaagcgga tccgcggcac cgacaacgtg gagccgaact tcaacgagat cgtggaggcg    780
agccgcatcg cgcaggaggt gaagcacccg ttccggaacc tgctccagcg ccggaaccgc    840
ccgcagctgg tcatcgccgt gctgctccag atcttccagc agttcacggg gatcaacgcc    900
atcatgttct acgcccccgt gctgttcaac acgctcgggt tcaagagcga cgcgtcgctc    960
tactcggcgg tgatcacggg cgccgtcaac gtgctggcca cgctggtgtc ggtgtacgcg   1020
gtggaccgcg ccgggcggcg cgcgctgctg ctggaggctg gcgtgcagat gttcctgtcg   1080
caggtggtga tcgccgtggt gctgggcatc aaggtgacgg acaagtcgga caacctgggc   1140
cacgggtggg ccatcctgtt ggtggtcatg gtgtgcacct acgtggcctc cttcgcctgg   1200
tcctggggcc cgctggggtg gctcatcccc agcgagacgt tcccgctgga gacgcggtcg   1260
gcggggcaga gcgtgacggt gtgcgtcaac ctgctcttca ccttcctcat cgcgcaggcc   1320
ttcctctccca tgctctgcca cctcaagttc gccatcttca tcttcttctc ggcctgggtg   1380
ctcgtcatgt ccgtcttcgt gctcttcttc ctcccggaga ccaagaacgt gcccatcgag   1440
gagatgaccg acaaggtgtg gaagcagcac tggttctgga gagattcat ggacgacgac    1500
gaccaccacc acaacatcgc caacggcaag aacgccaccg tctga                   1545
```

SEQ ID NO: 3　　　　　　　moltype = DNA　length = 1650
FEATURE　　　　　　　　　Location/Qualifiers
source　　　　　　　　　　1..1650
　　　　　　　　　　　　　mol_type = other DNA
　　　　　　　　　　　　　organism = Triticum aestivum
SEQUENCE: 3

```
tcctcgtgtg cttctgtgga gaaacactcg ctgcttgtct agcttccatt atatcggcgt     60
agcttgaccg gccggcttgc gaagatgccg ggcgggggggt tcgccgtgtc ggcgccgtcc    120
ggcgtggagt tcgaggccaa gatcacgccc atcgtcatca tctcctgcat catggcggcc    180
accggcggcc tcatgttcgg ctacgacgtc ggcatctcag gcgagtgac atcgatggac     240
gatttcctgc gtgagttctt cccggcggtg ctgcgccgaa agaaccagga caaggagagc    300
aactactgca agtacgacaa ccagggcctg cagctcttca cctcgtcgct ctacctcgcg    360
ggctcaccg ccaccttctt cgcctcctac accaccgcc gcctcggacg ccgcctcacc      420
atgctcatcg ccggcgtctt cttcatcatc ggcgtcatct tcaacggggc cgcccagaac    480
ctcgccatgc tcatcatcgg caggatcctg cttcgttgcg gcgtcggctt cgccaaccag    540
gccgttcccc tgttcctgtc ggagatcgcg ccgacgagga tccgcggcgg gctcaacatc    600
ctgttccagc tgaacgtgac catcggcatc ctgttcgcga acctggtgaa ctacggcacg    660
agcaagatcc accgtggggg ctggcggctg tcgctgtcgc tggccggcat cccggcggcc    720
atgctcaccc tgggcgcgct cttcgtcacc gacaccccca acagcctcat cgagcgcggc    780
cacctggagg agggcaaggc ggtgctcaag cggatccgca acgtgacga cgtggagccg    840
gagttcaacg agatcgtgga ggcgagccgc atcgcgcagg aggtgaagca cccgttccgg    900
aacctgctcc agcgccggaa ccgccgcag ctggtcatcg ccgtgctgct ccagatcttc      960
cagcagttca cggggatcaa cgccatcatg ttctacgccc ccgtgctgtt caacacgctc   1020
gggttcaaga gcgacgcgtc gctctactcg gcggtgatca cgggcgccgt caacgtgctg   1080
gccacgctgg tgtcggtgta cgccgtggac cgcgccgggc ggcgcgcgct gctggaggct  1140
ggcgtgcagc agatgttcct gtcgcaggtg gtgatcgccg tggtgctggg catcaaggtg   1200
acggacaagt cggacaacct gggccacggg tgggccatcc tgttggtggt catggtgtgc   1260
acctacgtgg cctccttcgc ctggtcctgg ggcccgctgg ggtggctcat ccccagcgag   1320
acgttcccgc tggagacgcg gtcggcgggg cagagcgtga cggtgtgcgt caacctgctc   1380
ttcaccttcc tcatcgcgca ggccttcctc tccatgctct gccacctcaa gttcgccatc   1440
ttcatctttct ctcggcctg gtgctcgtc atgtccgtct tcgtgctctt cttcctcccg   1500
gagaccaaga acgtgcccat cgaggagatg accgacaagg tgtggaagca gcactggttc   1560
tggaagagat tcatggacga cgacgaccac caccacaaca tcgccaacgg caagaacgcc   1620
accgtctgaa aagtgttgct cctactatgt                                    1650
```

SEQ ID NO: 4　　　　　　　moltype = AA　length = 514
FEATURE　　　　　　　　　Location/Qualifiers
source　　　　　　　　　　1..514
　　　　　　　　　　　　　mol_type = protein
　　　　　　　　　　　　　organism = Triticum aestivum
SEQUENCE: 4

```
MPGGGFAVSA PSGVEFEAKI TPIVIISCIM AATGGLMFGY DVGISGGVTS MDDFLREFFP     60
AVLRRKNQDK ESNYCKYDNQ GLQLFTSSLY LAGLTATFFA SYTTRRLGRR LTMLIAGVFF   120
IIGVIFNGAA QNLAMLIIGR ILLGCGVGFA NQAVPLFLSE IAPTRIRGGL NILFQLNVTI   180
GILFANLVNY GTSKIHPWGW RLSLSLAGIP AAMLTLGALF VTDTPNSLIE RGHLEEGKAV   240
LKRIRGTDNV EPEFNEIVEA SRIAQEVKHP FRNLLQRRNR PQLVIAVLLQ IFQQFTGINA   300
IMFYAPVLFN TLGFKSDASL YSAVITGAVN VLATLVSVYA VDRAGRRALL LEAGVQMFLS   360
QVVIAVVLGI KVTDKSDNLG HGWAILVVVM VCTYVASFAW SWGPLGWLIP SETFPLETRS   420
AGQSVTVCVN LLFTFLIAQA FLSMLCHLKF AIFIFFSAWV LVMSVFVLFF LPETKNVPIE   480
EMTDKVWKQH WFWKRFMDDD DHHHNIANGK NATV                                514
```

SEQ ID NO: 5　　　　　　　moltype = DNA　length = 1545
FEATURE　　　　　　　　　Location/Qualifiers
source　　　　　　　　　　1..1545
　　　　　　　　　　　　　mol_type = other DNA
　　　　　　　　　　　　　organism = Triticum aestivum
SEQUENCE: 5

```
atgccgggcg gggggttcgc cgtgtcggcg ccgtccggcg tggagttcga ggccaagatc     60
acgcccatct catcatctc ctgcatcatg gcggccaccg gcggcctcat gttcggctac    120
gacgtcggca tctcaggcgg agtgacatcg atggacgatt tcctgcgtga gttcttcccg    180
```

```
gcggtgctgc gccggaagaa ccaggacaag gagagcaact actgcaagta cgacaaccag   240
ggcctgcagc tcttcacctc gtcgctctac ctcgccggcc tcaccgccac cttcttcgcc   300
tcctacacca cccgccgcct cggacgccgc ctcaccatgc tcatcgccgg cgtcttcttc   360
atcatcggcg tcatcttcaa cggggccgcc cagaacctcg ccatgctcat catcggcagg   420
atcctgcttg gttgcggcgt cggcttcgcc aaccaggcgg ttcccctgtt cctgtcggaa   480
atcgcgccga cgaggatccg cggcgggctc aacatcctgt tccagctgaa cgtgaccatc   540
ggcatcctgt tcgcgaacct ggtgaactac ggcacgagca agatccaccc gtggggctgg   600
cggctgtcgc tgtcgctggc cggcatcccg cggcgatgc tcaccctggg cgcgctcttc   660
gtcaccgaca cccccaacag cctcatcgag gcgggccacc tggaggaggg caaggcggtg   720
ctcaagcgga tccgcggcac cgacaacgtg gagccggagt tcaacgagat cgtggaggcg   780
agccgcatcg cgcaggaggt gaagcacccg ttcggaaacc tgctccagcg cccggaaccgc   840
ccgcagctgg tcatcgccgt gctgctccag atcttccagc agttcacggg gatcaacgcc   900
atcatgttct acgcccccgt gctgttcaac acgctcgggt tcaagagcga cgccgtcgtc   960
tactcggcgg tgatcacggg cgtcgtcaac gtgctggcca cgctggtgtc ggtgtacgcg   1020
gtggaccgcg ccgggcggcg cgcgctgctg ctggaggctg gcgtgcagat gttcctgtcg   1080
caggtggtga tcgccgtggt gctgggcatc aaggtgacgg acaagtcgga caacctgggc   1140
cacgggtggg ccatcctggt ggtggtcatg gtgtgcacct acgtggcctc cttcgcctgg   1200
tcctggggcc cgctgggtg gctcatcccc agcgagacgt tcccgctgga gacgcggtcg   1260
gcggggcaga gcgtgacggt gtgcgtcaac ctgctcttca ccttcctcat cgcgcaggcc   1320
ttcctctcca tgctctgcca cctcaagttc gccatcttca tcttcttctc ggcctgggtg   1380
ctcgtcatgt ccgtcttcgt gctcttcttc ctcccggaga ccaagaacgt gcccatcgag   1440
gagatgaccg acaaggtgtg gaagcagcac tggttctgga agagattcat ggacgacgac   1500
gaccaccacc acaacatcgc caacggcaag aacgccaccg tctga                    1545

SEQ ID NO: 6              moltype = DNA  length = 1650
FEATURE                   Location/Qualifiers
source                    1..1650
                          mol_type = other DNA
                          organism = Triticum aestivum
SEQUENCE: 6
tcctcgtgtg cttctgtgga gaaacactcg ctgcttgtct agcttccatt atatcggcgt   60
agcttgaccg gccggcttgc gaagatgccg ggcggggggt tcgccgtgtc ggcgccgtcc   120
ggcgtggagt tcgaggccaa gatcacgccc atcgtcatca tctcctgcat catggcggcc   180
accggcggcc tcatgttcgg ctacgacgtc ggcatctcag gcggagtgac atcgatggac   240
gatttcctgc gtgagttctt ccccgtggtg ctgcgccgga agaaccagga caaggagagc   300
aactactgca gtacgacaa ccagggcctg cagctcttca cctcgtcgct ctacctcgcc   360
ggcctcaccg ccaccttctt cgcctcctac accacccgcc gcctcggacg ccgcctcacc   420
atgctcatcg ccggcgtctt cttcatcatc ggcgtcatct tcaacggggc cgcccagaac   480
ctcgccatgc tcatcatcgg caggatcctg cttggttgcg gcgtcggctt cgccaaccag   540
gccgttcccc tgttcctgtc ggagatcgcg ccgacgagga tccgcggcgg gctcaacatc   600
ctgttccagc tgaacgtgac catcggcatc ctgttcgcga acctggtgaa ctacggcacg   660
agcaagatcc accgtgggg ctgcggctg tcgctgtcgc tggccggcat cccggcggcg   720
atgctcaccc tgggcgcgct cttcgtcacc gacacccca acagcctcat cgaggcgggc   780
cacctggagg agggcaaggc ggtgctcaag cggatccgcg gcaccgacaa cgtggagccg   840
gagttcaacg agatcgtgga ggcgagccgc atcgcgcagg aggtgaagca cccgttccgg   900
aacctgctcc agcgccggaa ccgccgcag ctggtcatcg ccgtgctgct ccagatcttc   960
cagcagttca cggggatcaa cgccatcatg ttctacgccc ccgtgctgtt caacacgctc   1020
gggttcaaga gcgacgcgtc gctctactcg gcggtgatca cgggcgccgt caacgtgctg   1080
gccacgctgg tgtcggtgta cgccgtggac cgcgccgggc ggcgcgcgct gctgctggag   1140
gctggcgtgc agatgttcct gtcgcaggtg gtgatcgccg tggtgctggg catcaaggtg   1200
acggacaagt cggacaacct gggccacggg tgggccatcc tggtggtggt catgtgtgc   1260
acctacgtgg cctccttcgc ctggtcctgg ggcccgctgg gtggctcat ccccagcgag   1320
acgttcccgc tggagacgcg gtcgcgggg cagagcgtga cggtgtgcgt caacctgctc   1380
ttcaccttcc tcatcgcgca ggccttcctc tccatgctct gccacctcaa gttcgccatc   1440
ttcatcttct tctcggcctg ggtgctcgtc atgtccgtct tcgtgctctt cttcctcccg   1500
gagaccaaga acgtgcccat cgaggagatg accgacaagg tgtggaagca gcactggttc   1560
tggaagagat tcatggacga cgacgaccac caccacaaca tcgccaacgg caagaacgcc   1620
accgtctgaa aagtgttgct cctactatgt                                    1650

SEQ ID NO: 7              moltype = AA  length = 526
FEATURE                   Location/Qualifiers
source                    1..526
                          mol_type = protein
                          organism = Arabidopsis thaliana
SEQUENCE: 7
MTGGGFATSA NGVEFEAKIT PIVIISCIMA ATGGLMFGYD VGVSGGVTSM PDFLEKFFPV     60
VYRKVVAGAD KDSNYCKYDN QGLQLFTSSL YLAGLTATFF ASYTTRTLGR RLTMLIAGVF    120
FIIGVALNAG AQDLAMLIAG RILLGCGVGF ANQAVPLFLS EIAPTRIRGG LNILFQLNVT    180
IGILFANLVN YGTAKIKGGW GWRLSLGLAG IPALLLTVGA LLVTETPNSL VERGRLDEGK    240
AVLRRIRGTD NVEPEFADLL EASRLAKEVK HPFRNLLQRR NRPQLVIAVA LQIFQQCTGI    300
NAIMFYAPVL FSTLGFGSDA SLYSAVVTGA VNVLSTLVSI YSVDKVGRRV LLLEAGVQMF    360
FSQVVIAIIL GVKVTDTSTN LSKGFAILVV VMICTYVAAF AWSWGPLGWL IPSETFPLET    420
RSAGQSVTVC VNLLFTFIIA QAFLSMLCHF KFGIFIFFSS WVLIMSVFVM FLLPETKNIP    480
IEEMTERVWK KHWFWARFMD DHNDHEFVNG EKSNGKSNGF DPSTRL                   526

SEQ ID NO: 8              moltype = AA  length = 515
FEATURE                   Location/Qualifiers
source                    1..515
                          mol_type = protein
```

```
                        organism = Oryza sativa
SEQUENCE: 8
MAGGFSVSGS GVEFEAKITP IVIISCIMAA TGGLMFGYDV GISGGVTSMD DFLREFFPTV     60
LKKKHEDKES NYCKYDNQGL QLFTSSLYLA GLTATFFASY TTRRLGRRLT MLIAGVFFIV    120
GVIFNGAAQN LAMLIVGRIL LGCGVGFANQ AVPLFLSEIA PTRIRGGLNI LFQLNVTIGI    180
LFANLVNYGT AKIHPWGWRL SLSLAGIPAA LLTLGALFVV DTPNSLIERG RLEEGKAVLR    240
KIRGTDNVEP EFNIEVEASR VAQEVKHPFR NLLQRRNRPQ LVIAVLLQIF QQFTGINAIM    300
FYAPVLFNTL GFKTDASLYS AVITGAVNVL STLVSVYSAD RVGRRMLLLE AGVQMFLSQV    360
AIAVVLGIKV TDRSDNLGHG WAIMVVVMVC TFVSSFAWSW GPLGWLIPSE TFPLETRSAG    420
QSVTVCVNLL FTFVIAQAFL SMLCHLKYAI FAFFSAWVVV MSLFVLFFLP ETKNIPIEEM    480
TERVWKQHWF WKRFMDDADK HHVVPNGGKS NGATV                               515

SEQ ID NO: 9            moltype = AA  length = 536
FEATURE                 Location/Qualifiers
source                  1..536
                        mol_type = protein
                        organism = Vitis vinifera
SEQUENCE: 9
MPAGGFAAPS AGGGDFEAKIT PIVIISCIMA ATGGLMFGYD VGVSGGVTSM DPFLKKFFPV    60
VYRKQHEELE SNYCKYDNQG LQLFTSSLYL AGLTSTFFAS YTTRSFGRKA TMLIAGIFFI   120
VGVVLNTAAQ DLAMLIIGRI LLGCGVGFAN QAVPLFLSEI APTRIRGGLN ILFQLNVTIG   180
ILFANLVNYG TAKIKGGWGW RVSLGLAGIP AVLLTVGSLL VVDTPNSLIE RGRLEEGKAV   240
LRKIRGTDKI EPEYQELLEA SRVAKLVKHP FRNLMQRRNR PQLIIAVALQ IFQQFTGINA   300
IMFYAPVLFD TLGFGSDASL YSAVITGAVN VLSTLVSVYS VDKVGRRLLL LEAGVQMFFS   360
QVVIAIILGI KVKDHSNNLH TGYAVLVVVL VCTFVAGFAW SWGPLGWLIP SETFPLETRS   420
AGQSVTVCVN LLFTFVIAQS FLSMLCHLKY GIFLFFSGWV FIMSFFVLFL LPETKNIPIE   480
EMTERVWKKH WLWKRFMDDH VEGFPVFGYN DEETVVNGSD KKRDGYGNGF DPSSQL       536

SEQ ID NO: 10           moltype = DNA  length = 4243
FEATURE                 Location/Qualifiers
source                  1..4243
                        mol_type = other DNA
                        organism = Triticum aestivum
SEQUENCE: 10
atgccgggcg gggggttcgc cgtgtcggcg ccgtccggcg tggagttcga ggccaagatc     60
acgcccatcg tcatcatctc ctgcatcatg gcggccaccg gcggcctcat gttcggctac    120
gacgtcggca tctcaggtaa cccgatactc cacatgtcta tgcaagttct tccagagatc    180
gatcatctcc gtccatgcat gtgcgtgcgt tgcgtgctcc cgtggtagct ctgagaaatc    240
atgtcaaatc cgccttacat gcatggttta gtgatccgta acgtcgccgt ccgcgcgtat    300
gaaagagagg agtttaattg actccatgga tatggatatg tgtttacttt gtggctgccg    360
tctctcgtct tcatatgacg aagcagataa ccacagataa ttgaaggaa gttaatgcaa    420
ttgatcctcc tcattaacta ccacgcaccg gccagctgat aatttagcac tttccagttt    480
actccattgt gaacactatc cggtttttctg gccaggatca tgtatatgc tcgcacttgt    540
gctagctgta tgattctagc tgcatataag aattaatatt atactgtatt tggaagaaac    600
tatataactg ctgccatctt gccaccgact actttgacag gctgttaagt caacccattt    660
gtacacctcc agatcacgtc tgatgcaaca aagctgtctt ttgtgtggac acgttgcctt    720
tgggtttagc atagtattac atgaattctt actaaactt ttttttgcgag atgaattctt    780
actaaaacta attaagaaaa tcttgtccat ttctttcaca gcgtccagct cgattaacaa    840
ccagttctaa ggtctaaaaa ctgttttgtt ttgcaggcgg agtgacatcg atggacgatt    900
tcctgcgtga gttcttcccg gcggtgctgc gccggaagaa ccaggacaag gagagcaact    960
actgcaagta cgacaaccag ggcctgcagc tcttcacctc gtcgctctac ctcgccgggc   1020
tcaccgccac cttcttcgcc tcctacacca cccgccgcct cggacgccgc ctcaccatgc   1080
tcatcgccgg cgtcttcttc atcatcgcg tcatcttcaa cggggccgcc cagaacctcg   1140
ccatgctcat catcggcagg atcctgcttg gttgcggcgt cggcttcgcc aaccaggtta   1200
gcacaaattt ccaccagctt cagaattgta tatttttttaa tatcagtaag caagattacg   1260
tacgtttacg cagcaacatt tgatatgtac gtactcctag gtaacttaag tcaaaaggtt   1320
ttggtagaaa ccgaagtcaa acatgtaaag ctagcggtgg ctggttttgag aaaatatgta   1380
cgtagcacgc acacgcacga gacataattt tccgcgctca cgaaaatgac gtaacccgtg   1440
tgcagttttct tccttgtttg ctggcaatca gtcaccgccc acggtagtat caaagaatct   1500
ttggaccaaa ctaaacctac tggtcctacc atttttcacg tccagattaa tactcttcta   1560
aatataaaat attgttgtat tttatactcc ctccgttcct aaatataaat ctttttagac   1620
attcaaatg aactacaaca tacgatgta tgtaggcata ttttagagtg tagattcact   1680
cattttgctc cgtattcggt cacttgttgg aaagacttat atttgggaac ggagggagta   1740
tgtactagct gcagtacgta tgtaggtaca tcgtatcccct cttatatttc ccggaattca   1800
ggggtcaaat gtacaaacca tgtgacggtg catgactcgt gttggcgcac gaggacacct   1860
tccattggtg gcatcgcctc acctctcgcg ataaactgt taagttccaa gattccgatg   1920
ctggccgcga ccccgagctt agaaattact ggaccaaatg gtaggagaag cttgggccaa   1980
gcaacaggtg ataggtgcac gcttgcagct tatccccttct gtttctcatg gttttactag   2040
tctctgcagc agcagagttt gctgtgtgg ctgccctct ctctcgttgt cccaagttga   2100
aatcaacttg gactagttgt agaatataca aacacagcag ctttggattc ttctgttttt   2160
ggctgtcgaa actttgattt taatagcgaa attgcttcac ggacgatact ttccgcacga   2220
tccgtgaacg attcttcctt cgcgtccaaa tctcatgctt gcacgcacgc tgtggcgctg   2280
tcatgtagga tcgttcaggc ctcgacgcaa atctatcgtt gtgtagcaa cacttttta   2340
gtagtagcaa gcaggcgcgg ttgttcacgt gtaggccaca cgggtcgcaa tatgaagcga   2400
gcctagctga tagagtagtt atacataaac ttaggcctgg accaaaattg tatctttgat   2460
gcttgacttg gaggtgcact tcgcttggat tcttctggtt cctccttgc gaacaccgg     2520
aaaaaaaaac aatgtgtcta tggactgtag acctcagagc ggggagcttt ctcgattgaa   2580
aatgccaaga atttgtgcgc tagtgatgca ttagattact acacgggatca aggcactgat   2640
tgagcatgag tttgcaaaatt atgcacacac taacatccaa aaaaaaaaac caaacgtact   2700
```

```
tgtataatat aaaggcgtct agactcaatt atactccgta cgaagcaggc aagacaacat  2760
gcatgtgtgc cagaacttag ctcgagtagg agtagatcat tagtccaaca atattttatt  2820
acttaattcc accgcttctg attaggccca ctgattaaga gattccgatg gtgataggtt  2880
ggtgcggttc tgacacttta attatacggt cacatgctaa ggtgatttt tttttacagt   2940
aggaaagcat gctaggtgat ttgttttagc atcccaagaa aaggaaagaa aaaaggggaa  3000
gagaacattc tggcccaatg ggcctcgttc aggccatctg cattttttt ttgcggggac   3060
aggccatctg catttgatga cccatttcgt gatttcccgt ctcagaattt cttcttacta  3120
tacatttcta acgaaacgaa caactgtggt gcaggccgtt ccctgttcc tgtcggagat   3180
cgcgccgacg aggatccgcg gcgggctcaa catcctgttc cagctgaacg tgaccatcgg  3240
catcctgttc gcgaacctgg tgaactacgg cacgagcaag atccaccgt ggggctggcg   3300
gctgtcgctg tcgctggccg gcatcccggc ggcgatgctc acctgggcg cgctcttcgt   3360
caccgacacc cccaacagcc tcatcgagcg cggccacctg gaggagggca aggcggtgct  3420
caagcggatc cgcggcaccg acaacgtgga gccggagttc aacgagatcg tggaggcgag  3480
ccgcatcgcg caggaggtga agcacccgtt ccggaaccctg ctccagccgc ggaaccgccc  3540
gcagctggtc atcgccgtgc tgctccagat cttccagcag ttcacgggga tcaacgccat  3600
catgttctac gcccccgtgc tgttcaacac gctcgggttc aagagcgacg cgtcgctcta  3660
ctcggcggtg atcacgggcg ccgtcaacgt gctggccacg ctggtgtcgg tgtacgccgt  3720
ggaccgcgcc gggcggccgg gcgtgctgct ggaggctggc gtgcagatgt tcctgtcgca  3780
ggtggtgatc gccgtggtgc tgggcatcaa ggtgacggac aagtcggaca acctgggcca  3840
cgggtgggcc atcctggtgg tggtcatggt gtgcacctac gtggcctcct tcgcctggtc  3900
ctggggcccg ctggggtggc tcatcccag cgagacgttc ccgctggaga cgcggtcggc   3960
ggggcagagc gtgacggtgt gcgtcaacct gctcttcacc ttcctcatcg cgcaggcctt  4020
cctctccatg ctctgccacc tcaagttcgc catcttcatc ttcttctcgg cctgggtgct  4080
cgtcatgtcc gtcttcgtgc tcttcttcct cccggagacc aagaacgtgc ccatcgagga  4140
gatgaccgac aaggtgtgga agcagcactg gttctggaag agattcatgg acgacgacga  4200
ccaccaccac aacatcgcca acggcaagaa cgccaccgtc tga                   4243
```

RUST RESISTANCE GENE

INCORPORATION-BY-REFERENCE OF MATERIAL ELECTRONICALLY SUBMITTED

A Sequence Listing is provided herewith as a Sequence Listing XML, "RICE-189CON4_SEQ_LIST" created on Dec. 14, 2022 and having a size of 23 KB. The contents of the Sequence Listing XML are incorporated by reference herein in their entirety.

FIELD OF THE INVENTION

The present invention relates to new transporter polypeptides, and genes encoding therefor, which can be used to confer upon a plant resistance to one or more biotrophic fungal pathogens.

BACKGROUND OF THE INVENTION

Numerous genes conferring resistance to pathogens have been identified and used in plant breeding. However, single-gene pathogen resistance in plants often becomes ineffective due to the emergence of new virulent races of the disease agent. In contrast, durable disease resistance in plants is generally thought to be controlled by multiple genes. A few rust resistance genes have been isolated and cloned from wheat (Feuillet et al., 2003; Huang et al., 2003; Cloutier et al., 2007) and other cereals (Collins et al., 1999; Brueggeman et al., 2002) and are predominantly from the nucleotide binding site-leucine rich repeat (NB-LRR) class of major resistance (R) genes. For example, three wheat R genes (Lr1, Lr10 and Lr21) that provide protection against the wheat leaf rust fungus, *Puccinia triticina*, have been cloned (Somers et al., 2004; Hayden et al., 2008; Manly et al., 2001). One exception is the barley Rpg1 rust resistance gene which encodes a protein kinase. These genes encode gene-for-gene resistance against single pathogens and generally lead to strong, hypersensitive responses in the plant tissues upon infection.

In contrast, rust resistance genes in wheat (*Triticum aestivum* L.) such as Lr34, located on the chromosome arm 7DS, confer a broad spectrum and durable adult plant resistance against several obligate biotrophic pathogens including fungi from the Ascomycetes and Basidiomycetes. These include leaf rust, stripe rust, stem rust and powdery mildew and therefore the Lr34 gene has been widely deployed in wheat breeding despite its weaker, non-hypersensitive response phenotype (Dyck, 1977 and 1987; German and Kolmer, 1992; Bossolini et al., 2006; Spielmeyer et al., 2008). Cultivars with the resistance locus Lr34 such as Frontana have had effective durable resistance to the leaf rust fungus *Puccinia triticina* Eriks (Dyck et al., 1966; Singh and Rajaram, 1994). To date, isolates of *P. triticina* with complete virulence to Lr34 have not been detected (Kolmer et al., 2003). The Lr34 gene was recently cloned and shown to encode a protein in the ABC transporter family (Krattinger et al., 2009), although its function as a transporter was not demonstrated. Lr34 resistance has remained genetically inseparable from the gene designated Yr18 that confers resistance to stripe rust (*P. striiformis*) (Singh, 1992; McIntosh, 1992). Co-segregation of Lr34/Yr18 with other traits such as leaf tip necrosis (Ltn1) in adult plant stage, powdery mildew (recently designated Pm38), tolerance to barley yellow dwarf virus (Bdv1) and spot blotch (*Bipolaris sorokiniana*) have been documented (Singh, 1992a,b; McIntosh, 1992; Joshi et al., 2004; Spielmeyer et al., 2005; Liang et al., 2006), and these phenotypes are all thought to be conferred by the Lr34 resistance polypeptide.

A second gene that confers broad spectrum, adult plant resistance against several obligate biotrophic pathogens is Lr67, located on chromosome 4DL in wheat, and found in a few wheat accessions such as RL6077 (Herrera-Foessel et al., 2011). In contrast to Lr34, the Lr67 gene has not been widely used to produce resistant cultivars for commercial wheat production. Although an initial report (Dyck et al., 1994) based on plant phenotypes suggested that the resistance gene in RL6077 might be a translocated Lr34, this was subsequently shown not to be the case (Herrera-Foessel et al., 2011). After mapping the gene in two segregating populations, Hiebert et al., (2010) designated the gene in RL6077 as Lr67. Although Lr67 also leads to leaf tip necrosis and provides a partial, broad spectrum, adult plant resistance to leaf rust and stripe rust like Lr34, these are clearly different genes.

There is a need to determine the molecular basis of genes such as Lr67 that provide quantitative non-race-specific, adult plant pathogen resistance-type or partial resistance to a broad spectrum of pathogens.

SUMMARY OF THE INVENTION

The present inventors have identified new transporter polypeptides, and genes encoding therefor, which can be used to confer upon a plant resistance to one or more biotrophic fungal pathogens.

In a first aspect, the present invention provides a recombinant cell comprising an exogenous polynucleotide encoding a polypeptide which is characterised by one or more or all of:

i) when expressed in a plant, the polypeptide confers upon the plant resistance to one or more biotrophic fungal pathogen(s), preferably to one or more or all of leaf rust, stripe rust, stem rust and powdery mildew, ii) when expressed in a cell, the polypeptide is not as active at transporting glucose across a membrane of the cell as a polypeptide which comprises amino acids having a sequence as provided in SEQ ID NO:4, iii) when expressed in a cell, the polypeptide is active as a sugar transporter, iv) the polypeptide comprises amino acids having a sequence as provided in SEQ ID NO:1 or an amino acid sequence which is at least 40% identical to SEQ ID NO:1 or a biologically active fragment thereof, and v) the polypeptide does not comprise a glycine at a position corresponding to amino acid number 144 of SEQ ID NO:1, preferably the polypeptide comprises an amino acid other than glycine at the position corresponding to amino acid number 144 of SEQ ID NO:1, wherein the polynucleotide is operably linked to a promoter capable of directing expression of the polynucleotide in the cell.

In a preferred embodiment, the polypeptide at least has features i) and iv), i), ii) and iv), ii) and iv), or iv) and v), more preferably features i), iv) and v), i), ii), iv) and v), or i), iv) and v).

In an embodiment, the one or more biotrophic fungal pathogen(s) is a rust or a mildew or both a rust and a mildew. Examples of biotrophic fungi include, but are not limited to, *Blumeria graminis* f. sp. *tritici*, *Fusarium graminearum*, *Bipolaris sorokiniana*, *Erysiphe graminis* f. sp. *tritici*, *Puccinia graminis* f. sp. *tritici*, *Puccinia striiformis*, *Puccinia hordei* and *Puccinia recondita* f. sp. *tritici*.

In an embodiment, the cell is a plant or yeast cell. More preferably, the cell is a plant cell. In an embodiment, the plant cell is a cereal plant cell such as a wheat plant cell. In another embodiment, the plant cell is a grape cell.

In an embodiment, the promoter directs gene expression in a leaf and/or stem cell.

Preferably, if the polypeptide does not comprise a glycine at a position corresponding to amino acid number 144 of SEQ ID NO:1, the polypeptide comprises an amino acid sequence which is at least 40% identical to one or more or all of SEQ ID NO's 1, 4 or 7 to 9, or a biologically active fragment of one or more thereof.

In a preferred embodiment, the polypeptide comprises an amino acid at the position corresponding to amino acid number 144 of SEQ ID NO:1, wherein the amino acid is selected from the group consisting of arginine, lysine and histidine.

In a further preferred embodiment, the polypeptide does not comprise a valine at a position corresponding to amino acid number 387 of SEQ ID NO:1, preferably the polypeptide comprises an amino acid other than valine at the position corresponding to amino acid number 387 of SEQ ID NO:1. More preferably, the polypeptide comprises an amino acid at the position corresponding to amino acid number 387 of SEQ ID NO:1, wherein the amino acid is selected from the group consisting of leucine, isoleucine, methionine, alanine and phenylalanine.

In an embodiment, the exogenous polynucleotide is integrated into the genome of the cell.

In a further embodiment, the polypeptide comprises amino acids having a sequence as provided in SEQ ID NO:1 or an amino acid sequence which is at least 80% identical, at least 90% identical, or at least 95% identical to SEQ ID NO:1, or a biologically active fragment thereof.

In an embodiment, the polypeptide comprises 12 transmembrane domains.

In another aspect, the present invention provides a transgenic plant comprising cells of the invention, wherein the transgenic plant is transgenic for the exogenous polynucleotide.

In a preferred embodiment, each of the somatic cells of the plant comprise the exogenous polynucleotide.

In a further preferred embodiment, the plant has enhanced resistance to one or more biotrophic fungal pathogen(s), preferably to a rust, a mildew or both a rust and a mildew, more preferably to one or more or all of leaf rust, stripe rust, stem rust and powdery mildew, when compared to an isogenic plant lacking the exogenous polynucleotide.

In a further embodiment, the plant has enhanced resistance to one or more biotrophic fungal pathogen(s) at the seedling stage of growth.

In another embodiment, the plant comprises one or more further exogenous polynucleotides encoding a plant pathogen resistance polypeptide other than an Lr67 polypeptide, preferably an Lr34 polypeptide, an Sr33 polypeptide or an Sr35 polypeptide. Further plant pathogen resistance polypeptides include, but are not limited to, Lr1, Lr3, Lr2a, Lr3ka, Lr11, Lr13, Lr16, Lr17, Lr18, Lr21, and LrB.

Preferably, the plant is a cereal plant. Examples of transgenic cereal plants of the invention include, but are not limited to wheat, barley, maize, rice, oats and triticale. In a particularly preferred embodiment, the plant is wheat. In another embodiment, the plant is a grapevine.

In an embodiment, the promoter directs gene expression in an aerial part of the plant such as the leaves and/or the stems.

Preferably, the plant is homozygous for the exogenous polynucleotide(s).

In a further embodiment, the plant is growing in a field.

Also provided is a population of at least 100 plants of the invention growing in a field.

In another aspect, the present invention provides a process for determining whether a polypeptide confers resistance or susceptibility to one or more biotrophic fungal pathogen(s), preferably a rust, a mildew or both a rust and a mildew, more preferably to one or more or all of leaf rust, stripe rust, stem rust and powdery mildew, comprising:

i) obtaining a polynucleotide operably linked to a promoter, the polynucleotide encoding the polypeptide, wherein the polypeptide comprises amino acids having a sequence as provided in SEQ ID NO:1 or an amino acid sequence which is at least 40% identical to one SEQ ID NO:1, or a biologically active fragment thereof, ii) introducing the polynucleotide into a plant, iii) determining whether the level of resistance or susceptibility to the one or more biotrophic fungal pathogen(s), preferably a rust, a mildew or both a rust and a mildew, more preferably to one or more or all of leaf rust, stripe rust, stem rust and powdery mildew, is increased or decreased relative to an isogenic plant lacking the polynucleotide, and iv) optionally, if the level of resistance or susceptibility is increased, selecting a polynucleotide encoding the polypeptide which when expressed confers resistance or susceptibility to the one or more biotrophic fungal pathogen(s), preferably a rust, a mildew or both a rust and a mildew, more preferably to one or more or all of leaf rust, stripe rust, stem rust and powdery mildew.

In an embodiment, one or more of the following apply to the process, a) the polynucleotide comprises nucleotides having a sequence as provided in SEQ ID NO:2 or SEQ ID NO:3, a sequence which is at least 40% identical to one or both of SEQ ID NO:2 and SEQ ID NO:3, or a sequence which hybridizes to one or both of SEQ ID NO:2 and SEQ ID NO:3, b) the plant is a cereal plant such as a wheat plant or grapevine plant, c) the polypeptide is a plant polypeptide or mutant thereof, and d) step ii) further comprises stably integrating the polynucleotide operably linked to a promoter into the genome of the plant e) the polypeptide is characterised by one or more of the features defined above in relation to a cell of the invention.

In another aspect, the present invention provides a substantially purified and/or recombinant polypeptide which is characterised by one or more or all of:

i) when expressed in a plant, the polypeptide confers upon the plant resistance to one or more biotrophic fungal pathogen(s), preferably a rust, a mildew or both a rust and a mildew, more preferably to one or more or all of leaf rust, stripe rust, stem rust and powdery mildew, ii) when expressed in a cell, the polypeptide is not as active at transporting glucose across a membrane of the cell as a polypeptide which comprises amino acids having a sequence as provided in SEQ ID NO:4, iii) when expressed in a cell, the polypeptide is active as a sugar transporter, iv) the polypeptide comprises amino acids having a sequence as provided in SEQ ID NO:1 or an amino acid sequence which is at least 40% identical to SEQ ID NO:1, or a biologically active fragment thereof, and v) the polypeptide does not comprise a glycine at a position corresponding to amino acid number 144 of SEQ ID NO:1, preferably the polypeptide comprises an amino acid other than glycine at the position corresponding to amino acid number 144 of SEQ ID NO:1.

In a preferred embodiment, the polypeptide is characterised by one or more of the features defined above in relation to a cell of the invention.

In another aspect, the polypeptide comprises amino acids having a sequence as provided in SEQ ID NO:1 or an amino acid sequence which is at least 80% identical, at least 90% identical, or at least 95% identical, to SEQ ID NO:1, or a biologically active fragment thereof.

In an embodiment, a polypeptide of the invention is a fusion protein further comprising at least one other polypeptide sequence. The at least one other polypeptide may be, for example, a polypeptide that enhances the stability of a polypeptide of the present invention, or a polypeptide that assists in the purification or detection of the fusion protein.

In a further aspect, the present invention provides an isolated and/or exogenous polynucleotide comprising nucleotides having a sequence as provided in SEQ ID NO:2 or SEQ ID NO:3, a sequence which is at least 40% identical to one or both of SEQ ID NO:2 and SEQ ID NO:3, a sequence encoding a polypeptide of the invention, or a sequence which hybridizes to one or both of SEQ ID NO:2 and SEQ ID NO:3.

In another aspect, the present invention provides a chimeric vector comprising the polynucleotide of the invention.

Preferably, the polynucleotide is operably linked to a promoter.

In a further aspect, the present invention provides a recombinant cell comprising an exogenous polynucleotide of the invention and/or a vector of the invention.

The cell can be any cell type such as, but not limited to, a plant cell, a bacterial cell, an animal cell or a yeast cell.

Preferably, the cell is a plant cell. More preferably, the plant cell is a cereal plant cell. Even more preferably, the cereal plant cell is a wheat cell. In another embodiment, the plant cell is a grape cell.

In a further aspect, the present invention provides a method of producing the polypeptide of the invention, the method comprising expressing in a cell or cell free expression system the polynucleotide of the invention.

Preferably, the method further comprises isolating the polypeptide.

In another aspect, the present invention provides a method of producing the cell of the invention, the method comprising the step of introducing the polynucleotide of the invention, or a vector of the invention, into a cell.

Preferably, the cell is a plant cell.

In another aspect, the present invention provides a method of producing a transgenic plant of the invention, the method comprising the steps of i) introducing a polynucleotide of the invention and/or a vector of the invention into a cell of a plant, ii) regenerating a transgenic plant from the cell, and iii) optionally harvesting seed from the plant, and/or iv) optionally producing one or more progeny plants from the transgenic plant, thereby producing the transgenic plant.

In another aspect, the present invention provides a method of producing a plant which has integrated into its genome a polynucleotide encoding a polypeptide of the invention, the method comprising the steps of i) crossing two parental plants, wherein at least one plant comprises a polynucleotide encoding the polypeptide, ii) screening one or more progeny plants from the cross for the presence or absence of the polynucleotide, and iii) selecting a progeny plant which comprise the polynucleotide, thereby producing the plant.

In an embodiment, the polypeptide comprises amino acids having a sequence as provided in SEQ ID NO:1 or an amino acid sequence which is at least 40% identical to SEQ ID NO:1, or a biologically active fragment thereof, and wherein when expressed in the plant, the polypeptide confers upon the plant resistance to one or more biotrophic fungal pathogen(s), preferably a rust, a mildew or both a rust and a mildew, preferably to one or more or all of leaf rust, stripe rust, stem rust and powdery mildew.

In an embodiment, at least one of the parental plants is a tetraploid or hexaploid wheat plant. In another embodiment, the parental plant is a grapevine.

In another embodiment, step ii) comprises analysing a sample comprising DNA from the plant for the polynucleotide.

In a further embodiment, step iii) comprises i) selecting progeny plants which are homozygous for the polynucleotide, and/or ii) analysing the plant or one or more progeny plants thereof for resistance to one or more biotrophic fungal pathogen(s), preferably a rust, a mildew or both of a rust and a mildew, more preferably to one or more or all of leaf rust, stripe rust, stem rust and powdery mildew.

In another embodiment, the method further comprises iv) backcrossing the progeny of the cross of step i) with plants of the same genotype as a first parent plant which lacked a polynucleotide encoding the polypeptide for a sufficient number of times to produce a plant with a majority of the genotype of the first parent but comprising the polynucleotide, and iv) selecting a progeny plant which has resistance to one or more biotrophic fungal pathogen(s), preferably a rust, a mildew or both a rust and a mildew, more preferably to one or more or all of leaf rust, stripe rust, stem rust and powdery mildew.

In an embodiment, the method further comprises the step of analysing the plant for at least one other genetic marker.

Also provided is a plant produced using the method of the invention.

In another aspect, the present invention provides for the use of the polynucleotide of the invention, or a vector of the invention, to produce a recombinant cell and/or a transgenic plant.

In an embodiment, the transgenic plant has enhanced resistance to one or more biotrophic fungal pathogen(s), preferably a rust, a mildew or both a rust and a mildew, more preferably to one or more or all of leaf rust, stripe rust, stem rust and powdery mildew, when compared to an isogenic plant lacking the exogenous polynucleotide and/or vector.

In a further aspect, the present invention provides a method for identifying a plant comprising a polynucleotide encoding a polypeptide of the invention, the method comprising the steps of i) obtaining a nucleic acid sample from a plant, and ii) screening the sample for the presence or absence of the polynucleotide.

In an embodiment, the presence of the polynucleotide indicates that the plant has enhanced resistance to one or more biotrophic fungal pathogen(s), preferably a rust, a mildew or both a rust and a mildew, more preferably to one or more or all of leaf rust, stripe rust, stem rust and powdery mildew, when compared to an isogenic plant lacking the exogenous polynucleotide.

In an embodiment, a genomic region encompassing the polynucleotide is amplified and the amplification product sequenced to determine if it encodes the polypeptide. Primers useful for the amplification, and useful for the sequencing, can readily be designed by the skilled person.

In a further embodiment, the method identifies a transgenic plant of the invention.

In embodiment, the method further comprises producing a plant from a seed before step i).

Also provided is a plant part of the plant of the invention.

In an embodiment, the plant part is a seed that comprises an exogenous polynucleotide which encodes a polypeptide of the invention.

In a further aspect, the present invention provides a method of producing a plant part, the method comprising,
a) growing a plant of the invention, and
b) harvesting the plant part.

In another aspect, the present invention provides a method of producing flour, wholemeal, starch or other product obtained from seed, the method comprising:
a) obtaining seed of the invention, and
b) extracting the flour, wholemeal, starch or other product.

In a further aspect, the present invention provides a product produced from a plant of the invention and/or a plant part of the invention.

In an embodiment, the part is a seed.

In an embodiment, the product is a food product or beverage product. Examples include, but are not limited to;
i) the food product being selected from the group consisting of: flour, starch, leavened or unleavened breads, pasta, noodles, animal fodder, breakfast cereals, snack foods, cakes, malt, beer, pastries and foods containing flour-based sauces, or
ii) the beverage product being beer or malt.

In an alternative embodiment, the product is a non-food product. Examples include, but are not limited to, films, coatings, adhesives, building materials and packaging materials.

In a further aspect, the present invention provides a method of preparing a food product of the invention, the method comprising mixing seed, or flour, wholemeal or starch from the seed, with another food ingredient.

In another aspect, the present invention provides a method of preparing malt, comprising the step of germinating seed of the invention.

Also provided is the use of a plant of the invention, or part thereof, as animal feed, or to produce feed for animal consumption or food for human consumption.

In a further aspect, the present invention provides a composition comprising one or more of a polypeptide of the invention, a polynucleotide of the invention, a vector of the invention, or a recombinant cell of the invention, and one or more acceptable carriers.

In a further aspect, the present invention provides a method of identifying a compound that binds to a polypeptide comprising amino acids having a sequence as provided in SEQ ID NO:1 or an amino acid sequence which is at least 40% identical to SEQ ID NO:1, a biologically active fragment thereof, the method comprising:
i) contacting the polypeptide with a candidate compound, and
ii) determining whether the compound binds the polypeptide.

In an embodiment, the polypeptide is embedded in a cell membrane, preferably the membrane of a plant cell.

In a further aspect, the present invention provides a method of identifying a compound which is transported across a cell membrane by a polypeptide comprising amino acids having a sequence as provided in SEQ ID NO:1 or SEQ ID NO:4 or an amino acid sequence which is at least 40% identical to one or both of SEQ ID NO:1 or SEQ ID NO:4, or a biologically active fragment thereof, the method comprising:
i) contacting the polypeptide embedded in a cell membrane, preferably the membrane of a plant cell, with a candidate compound,
ii) determining whether the compound is transported from one side of the membrane to the other by the polypeptide.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1—Comparative genomics and mutant analysis.

Figure 2:

FIG. 2—Deleted Hsp70 gene is completely linked to Lr67.

Figure 3:
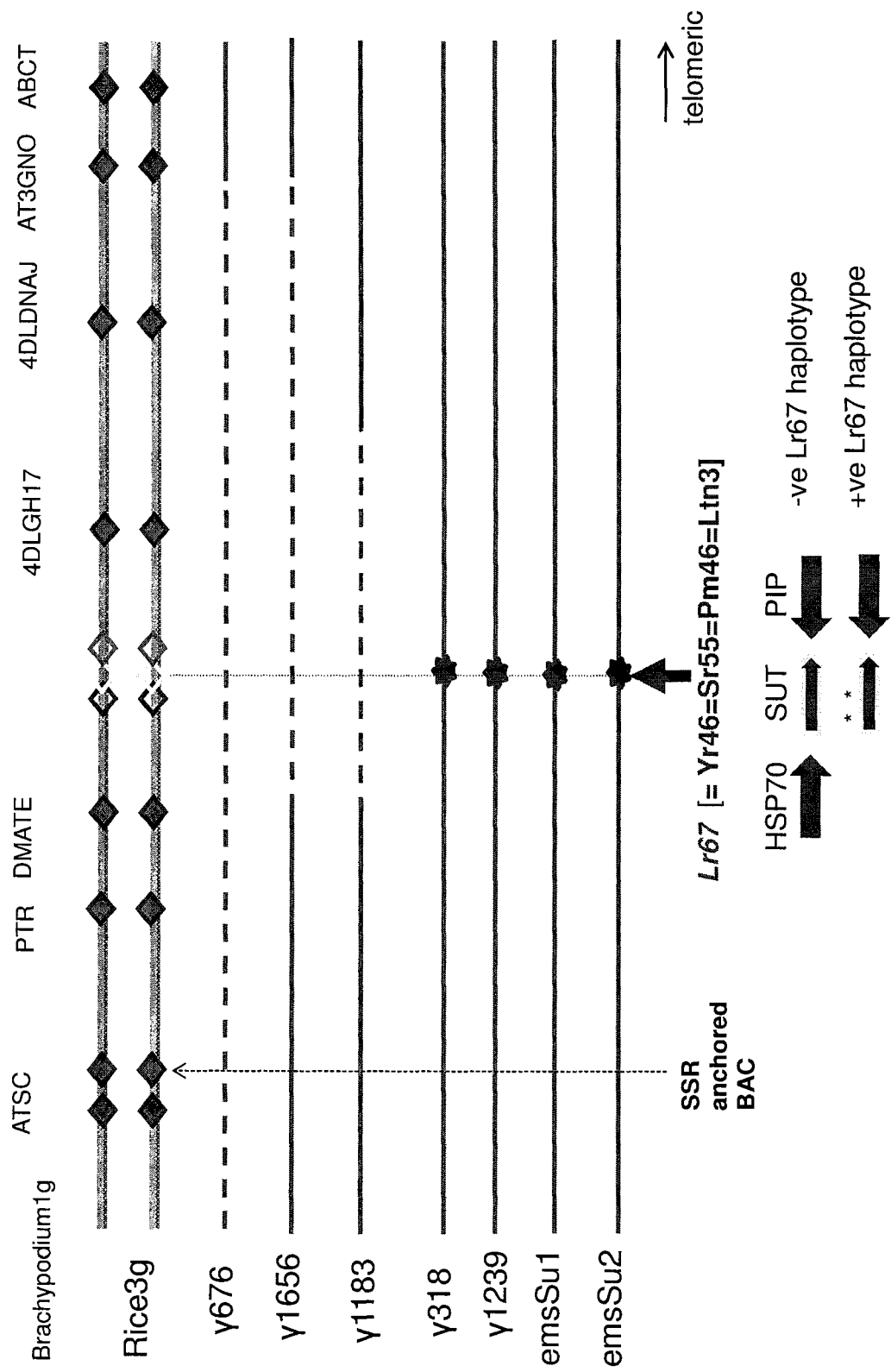

FIG. 3—Comparative genomics and mutant analysis including SUT and PIP.

Figure 4:
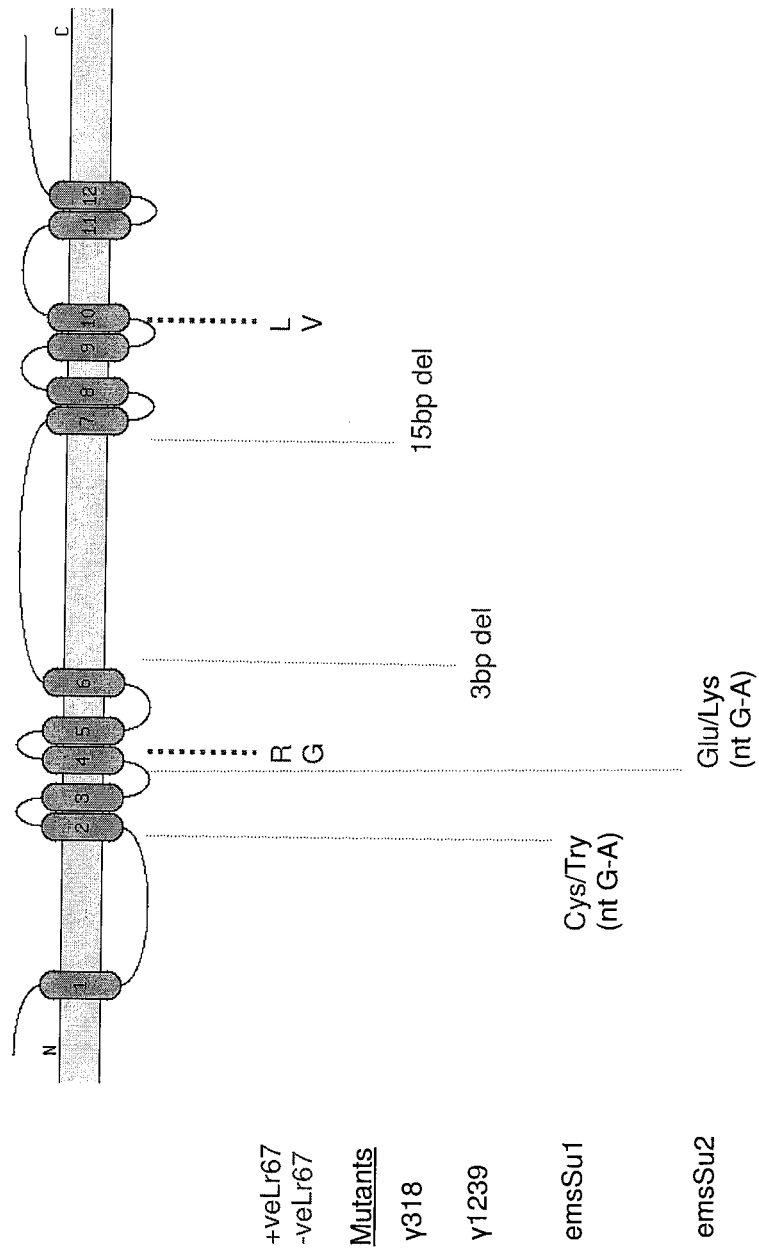

FIG. 4—Nucleotide changes found in Lr67 variants.

FIG. 5—Amino acid sequence (514 amino acids, SEQ ID NO:1) of the SUT polypeptide encoded by the Lr67 (resistant) allele of wheat. The arginine at position 144 in the predicted fourth trans-membrane domain and the leucine at position 387 distinguish the resistant Lr67 from the susceptible Lr67 polypeptide.

FIG. 6—Nucleotide sequence (SEQ ID NO:3) of the cDNA corresponding to the Lr67 resistant allele. Two SNP positions that distinguish+/−Lr67 are at positions 514 and 1243; these result in amino acid substitutions in the encoded polypeptides. The translation start codon is at position 85-87 and the translation stop codon is at position 1627-1629.

FIG. 7—Amino acid sequence (SEQ ID NO:4) of the Lr67 susceptible polypeptide (SUT).

FIG. 8—Nucleotide sequence (SEQ ID NO:6) of the cDNA corresponding to the Lr67 susceptible allele SUT.

FIG. 9—Alignment of the amino acid sequences of the wheat Lr67 (resistant) polypeptide (SEQ ID NO:1) with the homologous *Arabidopsis thaliana* polypeptide (Arath; from Genbank Accession No. NP_198006, 526 amino acids) (SEQ ID NO:7). Stars indicate an identical amino acid residue in that position, while "+" indicates a similar amino acid at that position.

FIG. 10—Alignment of the amino acid sequences of the wheat Lr67 (resistant) polypeptide (SEQ ID NO:1) with the homologous rice (*Oryza sativa*) polypeptide (Genbank Accession No. AAQ24871, 515 amino acids) (SEQ ID NO:8). Stars indicate an identical amino acid residue in that position, a "+" indicates a similar amino acid at that position.

Figure 11:
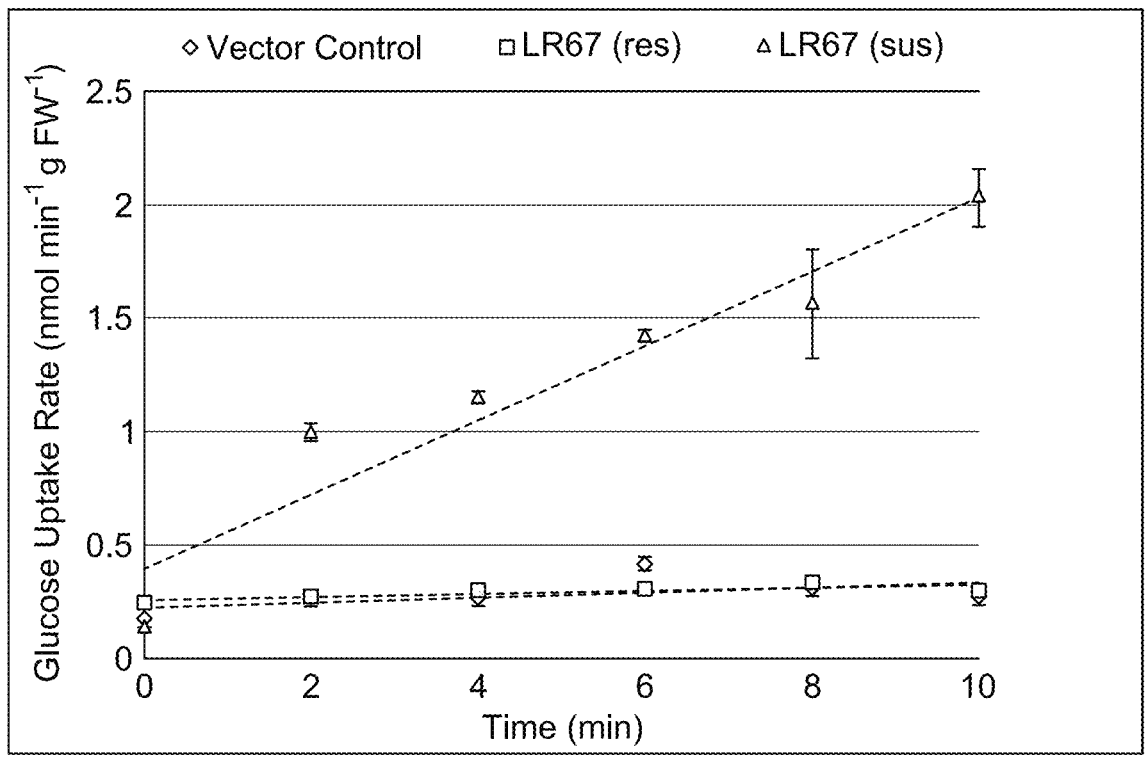

FIG. 11—Glucose uptake of yeast cells expressing Lr67 (resistant) and Lr67 (susceptible) proteins.

Figure 12:
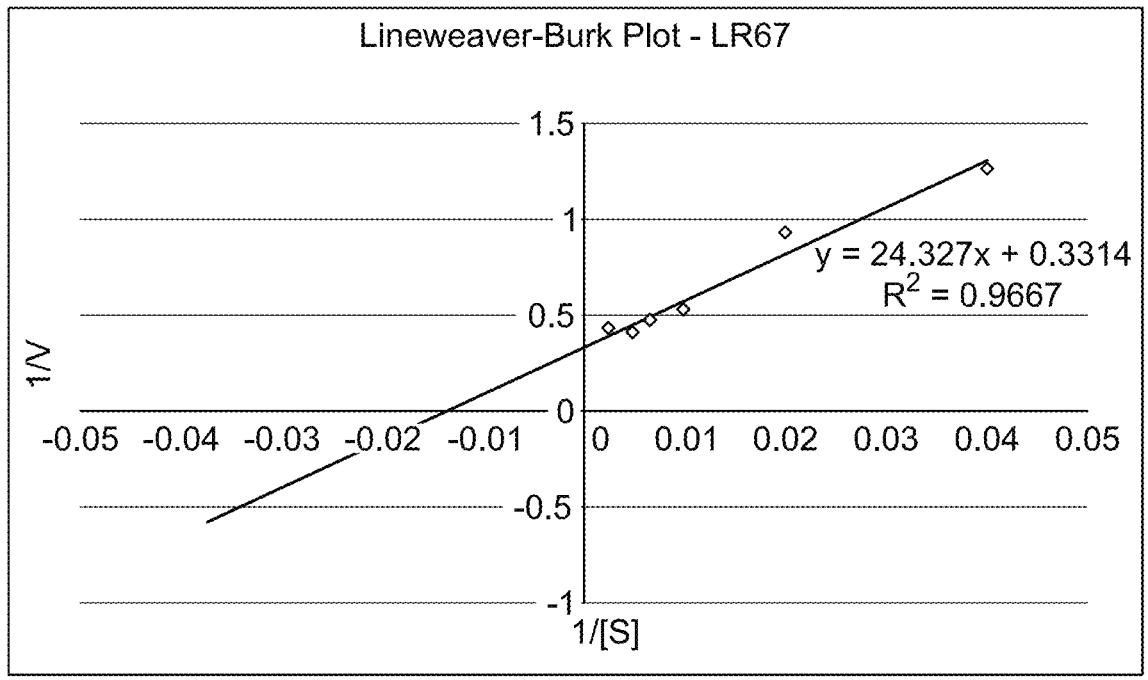

FIG. 12—Kinetics of glucose uptake in yeast expressing Lr67 (susceptible).

Figure 13:
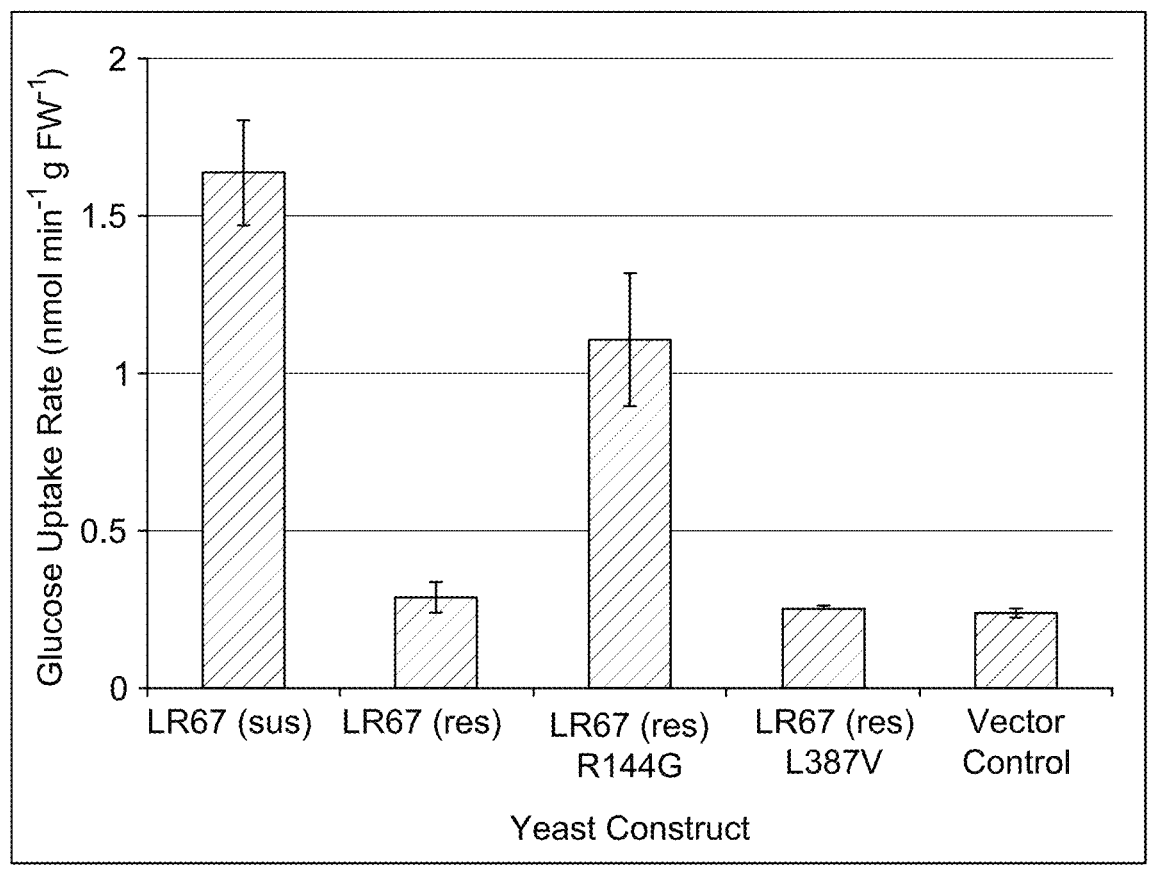

FIG. 13—Effect of variant amino acids on glucose transport by Lr67 proteins.

FIG. 14—Nucleotide sequence of a genomic fragment corresponding to the protein coding region of a Lr67 (susceptible) gene. The sequence starts with the translation start codon ATG and ends with the translation stop TGA. The two introns in the protein coding region are nucleotides 137-876 (Intron 1, 740 nt) and 1197-3154 (Intron 2, 1958 nt).

KEY TO THE SEQUENCE LISTING

SEQ ID NO:1—Wheat Lr67 (resistant) protein.
SEQ ID NO: 2—Open reading frame encoding wheat Lr67 (resistant) protein.
SEQ ID NO: 3—cDNA encoding wheat Lr67 (resistant) protein.
SEQ ID NO:4—Wheat Lr67 (susceptible) protein.
SEQ ID NO: 5—Open reading frame encoding wheat Lr67 (susceptible) protein.
SEQ ID NO: 6—cDNA encoding wheat Lr67 (susceptible) protein.
SEQ ID NO:7—*Arabidopsis thaliana* Lr67 protein.
SEQ ID NO:8—Rice (*Oryza sativa*) Lr67 protein.
SEQ ID NO:9—Grapevine (*Vitis vinifera*) Lr67 protein.
SEQ ID NO:10—Gene encoding wheat Lr67 (susceptible) protein.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Polypeptides

The present invention relates to polypeptides which, when expressed in a plant, confer upon the plant resistance to one or more biotrophic fungal pathogen(s), preferably to one or more or all of leaf rust, stripe rust, stem rust and powdery mildew. The present invention also relates to polypeptides which, when expressed in a cell, are not as active at transporting glucose across a membrane of the cell as a polypeptide which comprises amino acids having a sequence as provided in SEQ ID NO:4. In addition, the present invention also relates to polypeptides which, when expressed in a cell, act as a sugar transporter. In a preferred embodiment, the polypeptide is encoded by an allele or variant of an Lr67 gene which confers plant resistance to one or more biotrophic fungal pathogen(s). Examples of such polypeptides include, but are not limited to, those comprising an amino acid sequence as provided in SEQ ID NO:1. The polypeptide of the invention confers enhanced resistance to one or more biotrophic fungal pathogen(s) when compared to an isogenic plant lacking a polynucleotide encoding the polypeptide.

As used herein, the term "Lr67" relates to a protein family which share high primary amino acid sequence identity, for example at least 40%, least 80%, at least 90%, or at least 95% identity with one or more of the amino acid sequences provided as SEQ ID NO:1, 4 or 7 to 9, preferably SEQ ID NO:1. The present inventors have determined that some variants of the Lr67 protein family, when expressed in a plant, confer upon the plant resistance to one or more biotrophic fungal pathogen(s), preferably to one or more or all of leaf rust, stripe rust, stem rust and powdery mildew. An example of such a variant comprises an amino acid sequence provided as SEQ ID NO:1. Thus, variants which confer resistance are referred to herein as Lr67 (resistant) polypeptides, whereas those which do not (such as comprising the amino acid sequence provided as SEQ ID NO:4) are referred to herein as Lr67 (susceptible) polypeptides. In a preferred embodiment, Lr67 (resistant) proteins do not comprise a glycine at a position corresponding to amino acid number 144 of SEQ ID NO:1, preferably the polypeptide comprises an amino acid other than glycine at the position corresponding to amino acid number 144 of SEQ ID NO:1. The amino acid at position 144 is preferably a charged amino acid such as arginine, lysine or histidine.

As used herein, "resistance" is a relative term in that the presence of a polypeptide of the invention (i) reduces the disease symptoms of a plant comprising the gene (R (resistant) gene) that confers resistance, relative to a plant lacking the R gene, and/or (ii) reduces pathogen reproduction or spread on a plant or within a population of plants comprising the R gene. Resistance as used herein is relative to the "susceptible" response of a plant to the same pathogen. Typically, the presence of the R gene improves at least one production trait of a plant comprising the R gene when infected with the pathogen, such as grain yield, when compared to an isogenic plant infected with the pathogen but lacking the R gene. The isogenic plant may have some level of resistance to the pathogen, or may be classified as susceptible. Thus, the terms "resistance" and "enhanced resistance" are generally used herein interchangeably. Furthermore, a polypeptide of the invention does not necessarily confer complete pathogen resistance, for example when some symptoms still occur or there is some pathogen reproduction on infection but at a reduced amount within a plant or a population of plants. Resistance may occur at only some stages of growth of the plant, for example in adult plants (fully grown in size) and less so, or not at all, in seedlings, or at all stages of plant growth. By using a transgenic strategy to express an Lr67 polypeptide in a plant, the plant of the invention can be provided with resistance throughout its growth and development. Enhanced resistance can be determined by a number of methods known in the art such as analysing the plants for the amount of pathogen and/or analysing plant growth or the amount of damage or disease symptoms to a plant in the presence of the pathogen, and comparing one or more of these parameters to an isogenic plant lacking an exogenous gene encoding a polypeptide of the invention.

As used herein, a "sugar transporter" is a membrane bound protein which facilitates the movement of a sugar across a membrane, for example from outside of a cell into the cell, or in the opposite direction from inside a cell to outside, or across a membrane of a subcellular organelle within the cell. The facilitation may be active, using an energy source such as from an ionic gradient across the membrane, or passive. For Lr67 (susceptible) proteins the sugar can be glucose. In an embodiment, the sugar is a monosaccharide, preferably a hexose monosaccharide or a pentose polysaccharide. In an embodiment, the sugar may be modified such as a sugar alcohol or phosphorylated sugar.

As used herein, the phrase "not as active at transporting glucose across a membrane of the cell as a polypeptide which comprises amino acids having a sequence as provided in SEQ ID NO:4" means that the polypeptide of the invention has less than 50%, or less than 25%, or less than 10%, of the ability of a polypeptide which comprises amino acids having a sequence as provided in SEQ ID NO:4 to transport glucose into a cell such as a yeast or plant cell. This can readily be determined as described herein (see, for instance, FIG. 11 and associated experimental details).

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 90% free from other components with which it is naturally associated. In an embodiment, the polypeptide of the invention has an amino acid sequence which is different to a naturally occurring Lr67 polypeptide i.e. is an amino acid sequence variant.

Transgenic plants and host cells of the invention may comprise an exogenous polynucleotide encoding a polypeptide of the invention. In these instances, the plants and cells produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the cell comprises a non-endogenous gene that causes an altered amount of the polypeptide to be produced. In an embodiment, a "recombinant polypeptide" is a polypeptide made by the expression of an exogenous (recombinant) polynucleotide in a plant cell.

The terms "polypeptide" and "protein" are generally used interchangeably.

The % identity of a polypeptide is determined by GAP (Needleman and Wunsch, 1970) analysis (GCG program) with a gap creation penalty=5, and a gap extension penalty=0.3. The query sequence is at least 400 amino acids in length, and the GAP analysis aligns the two sequences over a region of at least 400 amino acids. More preferably, the query sequence is at least 500 amino acids in length and the GAP analysis aligns the two sequences over a region of at least 500 amino acids. Even more preferably, the GAP analysis aligns two sequences over their entire length, which for an Lr67 polypeptide is about 514 amino acid residues.

As used herein, a "biologically active fragment" is a portion of a polypeptide of the invention which maintains a defined activity of the full-length polypeptide such as one or both of i) when expressed in a plant, such as wheat, confers (enhanced) resistance to one or more biotrophic fungal pathogen(s), preferably to one or more or all of leaf rust, stripe rust, stem rust and powdery mildew, and ii) when expressed in a cell, the polypeptide is active as a sugar transporter, preferably not as active at transporting glucose across a membrane of the cell as a polypeptide which comprises amino acids having a sequence as provided in SEQ ID NO:4. Biologically active fragments can be any size as long as they maintain the defined activity but are preferably at least 400 or at least 500 amino acid residues long. Preferably, the biologically active fragment maintains at least 50%, at least 75% or at least 90%, of the activity of the full length protein. In an embodiment, the biologically active fragment comprises 12 transmembrane domains.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In an embodiment, a polypeptide of the invention is not a naturally occurring polypeptide such consisting of an amino acid sequence provided as SEQ ID NO:1 or SEQ ID NO:4.

As used herein, the phrase "at a position corresponding to amino acid number" or variations thereof refers to the relative position of the amino acid compared to surrounding amino acids. In this regard, in some embodiments a polypeptide of the invention may have deletional or substitutional mutation which alters the relative positioning of the amino acid when aligned against, for instance, SEQ ID NO:1. For example, as shown in FIG. 9 amino acid number 178 of wheat Lr67 (resistant) corresponds to amino acid number 179 of the homologous Lr67 protein from *Arabidopsis*.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have only one, two, three, four or less than 10 amino acid changes relative to the reference wildtype polypeptide.

Mutant (altered) polypeptides can be prepared using any technique known in the art, for example, using directed evolution or rational design strategies (see below). Products derived from mutated/altered DNA can readily be screened using techniques described herein to determine if they have one or more of the following features i) when expressed in a plant, such as wheat, confer (enhanced) resistance to one or more biotrophic fungal pathogen(s), preferably to one or more or all of leaf rust, stripe rust, stem rust and powdery mildew, ii) when expressed in a cell, the encoded polypeptide is not as active at transporting glucose across a membrane of the cell as a polypeptide which comprises amino acids having a sequence as provided in SEQ ID NO:4, and iii) when expressed in a cell, the polypeptide is active as a sugar transporter. For instance with regard to i), the method may comprise producing a transgenic plant expressing the mutated/altered DNA and determining the effect of the pathogen on the growth of the plant.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. Where it is derisible to maintain a certain activity it is preferable to make no, or only conservative substitutions, at amino acid positions which are highly conserved in the relevant protein family. Examples of conservative substitutions are shown in Table 1 under the heading of "exemplary substitutions".

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs which are highly conserved between the different polypeptides provided herewith, and/or not in the 12 transmembrane helices of the Lr67 polypeptides. As the skilled person would be aware, such minor changes can reasonably be predicted not to alter the activity of the polypeptide when expressed in a recombinant cell.

The primary amino acid sequence of a polypeptide of the invention can be used to design variants/mutants thereof based on comparisons with closely related sugar transporter polypeptides (for example, as shown in FIGS. 9 and 10). As the skilled addressee will appreciate, residues highly conserved amongst closely related proteins are less likely to be able to be altered, especially with non-conservative substitutions, and activity maintained than less conserved residues (see above).

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. The polypeptides may be post-translationally modified in a cell, for example by phosphorylation, which may modulate its activity. These modifications may serve to increase the stability and/or bioactivity of the polypeptide of the invention.

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Directed Evolution

In directed evolution, random mutagenesis is applied to a protein, and a selection regime is used to pick out variants that have the desired qualities, for example, increased activity. Further rounds of mutation and selection are then applied. A typical directed evolution strategy involves three steps:

1) Diversification: The gene encoding the protein of interest is mutated and/or recombined at random to create a large library of gene variants. Variant gene libraries can be constructed through error prone PCR (see, for example, Leung, 1989; Cadwell and Joyce, 1.992), from pools of DNaseI digested fragments prepared from parental templates (Stemmer, 1994a: Stemmer, 1994b; Crameri et al., 1998; Coco et al., 2001) from degenerate oligonucleotides (Ness et al., 2002, Coco, 2002) or from mixtures of both, or even from undigested parental templates (Zhao et al, 1998; Eggert et al., 2005; Jézéquek et al, 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the *E. coli* XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection: The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of activity.

3) Amplification: The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interactive Protein Redesign and Optimization), EGAD (A Genetic Algorithm for Protein Design), Rosetta Design, Sharpen, and Abalone.

Polynucleotides and Genes

The present invention refers to various polynucleotides. As used herein, a "polynucleotide" or "nucleic acid" or "nucleic acid molecule" means a polymer of nucleotides, which may be DNA or RNA or a combination thereof, and includes genomic DNA, mRNA, cRNA, and cDNA. Less preferred polynucleotides include tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid". Preferred polynucleotides of the invention encode a polypeptide of the invention.

By "isolated polynucleotide" we mean a polynucleotide which has generally been separated from the polynucleotide sequences with which it is associated or linked in its native state, if the polynucleotide is found in nature. Preferably, the isolated polynucleotide is at least 90% free from other components with which it is naturally associated, if it is found in nature. Preferably the polynucleotide is not naturally occurring, for example by covalently joining two shorter polynucleotide sequences in a manner not found in nature (chimeric polynucleotide).

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "Lr67 gene" as used herein refers to a nucleotide sequence which is homologous to an isolated Lr67 cDNA (such as provided in SEQ ID NO:3 and SEQ ID NO:6). As described herein, some alleles and variants of the Lr67 gene family encode a protein that confers resistance to one or more biotrophic fungal pathogen(s), preferably to one or more or all of leaf rust, stripe rust, stem rust and powdery mildew (see, for example, SEQ ID NO:3). Lr67 genes include the naturally occurring alleles or variants existing in cereals such as wheat, as well as artificially produced variants.

A genomic form or clone of a gene containing the transcribed region may be interrupted with non-coding sequences termed "introns" or "intervening regions" or "intervening sequences", which may be either homologous or heterologous with respect to the "exons" of the gene. An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. As described herein, the wheat Lr67 genes (both resistant and susceptible alleles) contain two introns in their protein coding regions. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or, preferably, for integration into the host genome.

As used herein, a "chimeric gene" refers to any gene that comprises covalently joined sequences that are not found joined in nature. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. In an embodiment, the protein coding region of an Lr67 gene is operably linked to a promoter or polyadenylation/terminator region which is heterologous to the Lr67 gene, thereby forming a chimeric gene. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell that does not naturally comprise the polynucleotide. The cell may be a cell which comprises a non-endogenous polynucleotide resulting in an altered amount of production of the encoded polypeptide, for example an exogenous polynucleotide which increases the expression of an endogenous polypeptide, or a cell which in its native state does not produce the polypeptide. Increased production of a polypeptide of the invention is also referred to herein as "over-expression". An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

The % identity of a polynucleotide is determined by GAP (Needleman and Wunsch, 1970) analysis (GCG program) with a gap creation penalty=5, and a gap extension penalty=0.3. The query sequence is at least 1,200 nucleotides in length, and the GAP analysis aligns the two sequences over a region of at least 1,200 nucleotides. Even more preferably, the query sequence is at least 1,500 nucleotides in length and the GAP analysis aligns the two sequences over a region of at least 1,500 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

The present invention also relates to the use of oligonucleotides, for instance in methods of screening for a polynucleotide of, or encoding a polypeptide of, the invention. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule.

The present invention includes oligonucleotides that can be used as, for example, probes to identify nucleic acid molecules, or primers to produce nucleic acid molecules. Probes and/or primers can be used to clone homologues of the polynucleotides of the invention from other species. Furthermore, hybridization techniques known in the art can also be used to screen genomic or cDNA libraries for such homologues.

Polynucleotides and oligonucleotides of the present invention include those which hybridize under stringent conditions to one or more of the sequences provided as SEQ ID NO's: 2, 3, 5 or 6. As used herein, stringent conditions are those that (1) employ low ionic strength and high temperature for washing, for example, 0.015 M NaCl/0.0015 M sodium citrate/0.1% NaDodSO$_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid). A variant of a polynucleotide or an oligonucleotide of the invention includes molecules of varying sizes of, and/or are capable of hybridising to, the wheat genome close to that of the reference polynucleotide or oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

Nucleic Acid Constructs

The present invention includes nucleic acid constructs comprising the polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is a stem-specific promoter, a leaf-specific promoter or a promoter which directs gene expression in an aerial part of the plant (at least stems and leaves) (green tissue specific promoter) such as a ribulose-1,5-bisphosphate carboxylase oxygenase (RUBISCO) promoter.

Examples of stem-specific promoters include, but are not limited to those described in U.S. Pat. No. 5,625,136, and Bam et al. (2008).

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a 0-glucuronidase (GUS) enzyme for which various chromogenic substrates are known, a 0-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a protein of the invention may be modulated by increasing the level of expression of a nucleotide sequence that codes for the protein in a plant cell, or decreasing the level of expression of a gene encoding the protein in the plant, leading to modified pathogen resistance. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of pathogen resistance or other phenotype. Alternatively, a population of mutagenized seed or a population of plants from a breeding program may be screened for individual lines with altered pathogen resistance or other phenotype associated with pathogen resistance.

Recombinant Cells

Another embodiment of the present invention includes a recombinant cell comprising a host cell transformed with one or more recombinant molecules of the present invention, or progeny cells thereof. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants".

A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "compared to an isogenic plant", or similar phrases, refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops); grapes; beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, triticale, oats or barley, even more preferably wheat.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed "breadwheat"). Tetraploid wheat includes *T. durum* (also referred to herein as durum wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu*, *T. monococcum* or *T. boeoticum* for the A genome, *Aegilops speltoides* for the B genome, and *T. tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

As used herein, the "other genetic markers" may be any molecules which are linked to a desired trait of a plant. Such markers are well known to those skilled in the art and include molecular markers linked to genes determining traits such disease resistance, yield, plant morphology, grain quality, dormancy traits, grain colour, gibberellic acid content in the seed, plant height, flour colour and the like. Examples of such genes are the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force.

Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265).

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. Nos. 5,004,863, 5,159,135, 5,518,908); soybean (U.S. Pat. Nos. 5,569,834, 5,416,011); *Brassica* (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one Lr67 allele or variant that confers upon the plant resistance to one or more biotrophic fungal pathogen(s), preferably to one or more or all of leaf rust, stripe rust, stem rust and powdery mildew, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of the (for example) Lr67 gene which confers upon the plant resistance to one or more biotrophic fungal pathogen(s), preferably to one or more or all of leaf rust, stripe rust, stem rust and powdery mildew. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., (2001).

In an embodiment, a linked loci for marker assisted selection is at least within 1 cM, or 0.5 cM, or 0.1 cM, or 0.01 cM from a gene encoding a polypeptide of the invention.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a Lr67 gene or allele which confers upon the plant resistance to one or more biotrophic fungal pathogen(s), preferably to one or more or all of leaf rust, stripe rust, stem rust and powdery mildew. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Plant/Grain Processing

Grain/seed of the invention, preferably cereal grain and more preferably wheat grain, or other plant parts of the invention, can be processed to produce a food ingredient, food or non-food product using any technique known in the art.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain, such as barley or wheat grain, of the invention, (ii) steeping said grain, (iii) germinating the steeped grains under predetermined conditions and (iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of specialty malts, including, but limited to, methods of roasting the malt.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

EXAMPLES

Example 1. The Lr67/Yr46 Gene is an Adult Plant Resistance Gene Distinct from Lr34/Yr18 and Lr46/Yr29

Introduction

Rust resistance genes in wheat are classified into two broad categories which are referred to as seedling and adult plant resistance (APR) genes. Seedling resistance genes are detected phenotypically after challenge of the plant with the rust pathogen and are observed during both the seedling and adult plant stages; as such they confer a resistance phenotype during all stages of plant growth. In contrast, APR is generally not observed at the seedling stage but instead is detected at the post-seedling stage of growth and often as resistance to the pathogen in plants growing in the field. In a few exceptions, some APR genes can be induced to express in seedlings by varying the growth temperature and light conditions, but are not expressed in seedlings under all growth conditions. Additionally, seedling resistance genes typically exhibit phenotypes of major effect and with varying infection types whereas most of the APR genes are partial in effect with varying levels of disease severity. Race specificity is more common with the seedling resistance genes. Of the few APR genes that have been studied in wheat, most appear to be race non-specific and a limited number are clearly race specific. Those of the race non-specific class with partial resistance are associated with a slow rusting phenotype first described by Caldwell (1968). Typically, slow rusting resistance shows longer latent periods, fewer uredinia and smaller uredinia sizes within the first two weeks post inoculation when compared to susceptible plants.

One of the well characterised race non-specific resistance genes is the adult plant leaf rust resistance gene Lr34 (WO2010/022443). Earlier referred to as LrT2 (Dyck 1977, 1987) it is present in older South American wheat cultivars such as Frontana and its derivatives, some of the early crossbred wheat cultivars at the beginning of last century and some wheat landraces (non-cultivated varieties isolated from wild-grown wheats) in particular those of Chinese origin (Borghi 2001; Kolmer et al., 2008). An important feature of Lr34 was that virulence in the wheat leaf rust pathogen has not been reported to date, and the enhanced effect of rust resistance when the Lr34 gene was combined in wheat cultivars with other race specific leaf rust resistance genes has contributed to the durability of wheat cultivars with Lr34 gene combinations (Kolmer, 1996). However, variability in the extent of rust colony development between leaf rust isolates on Lr34 has been reported (Bender and Pretorius, 2000). Co-segregation of Lr34 with the adult plant stripe rust resistance gene Yr18 (McIntosh 1992; Singh 1992) in exhibiting dual rust resistance in numerous wheat backgrounds may have contributed to the continued widespread use of the Lr34/Yr18 germplasm in wheat breeding. Subsequent observations that the Lr34/Yr18 locus also contributed to partial resistance against adult plant powdery mildew (Pm38) highlighted the multi-pathogen nature of the Lr34/Yr18/Pm38 locus on the short arm of wheat chromosome 7D (Spielmeyer et al., 2005; Lillemo et al., 2008).

Chemical and physical mutagenesis were used to investigate the multi-pathogen resistance locus containing Lr34 on wheat chromosome 7DS (Spielmeyer et al., 2008). Susceptible mutants were recovered for which there was no loss of DNA markers in the QTL interval on 7DS. These mutants were subsequently shown to be point mutations of which the chemical mutagen had created single base substitutions. Additional mutants generated by gamma irradiation had single base deletions within a gene encoding an ATP Binding Cassette (ABC) transporter at the multi-pathogen resistance locus (Krattinger et al., 2009). In addition to the ABC transporter, six other genes co-segregated with the resistance locus and were genetically and physically closely linked. However none of the mutants (eight independent mutants) had changes in the additional genes. Thus mutagenic changes to the ABC transporter alone were adequate to confer loss of all three of the leaf rust, stripe rust and powdery mildew resistances encoded by Lr34/Yr18/Pm38. Together with haplotype analysis and high resolution mapping, it was established that a single gene, an ABC transporter, conferred all three resistances (Krattinger et al., 2009).

Lr67/Yr46 is Distinct from Lr34/Yr18 and Lr46/Yr29

In the course of developing near isogenic lines for leaf rust resistance in the cultivar Thatcher, Dyck (1987) observed a phenotypic spectrum in line RL6077 (Thatcher*6/PI250413), that was similar to RL6058, a near-isogenic line carrying Lr34/Yr18. In subsequent studies, the APR in RL6077 segregated independently of Lr34/Yr18 and there was evidence for a translocation difference between the lines. As a result Dyck et al. (1994) inferred that RL6077 was a carrier of the Lr34/Yr18 gene, but on a different chromosome to 7DS. With the development of closely linked genetic markers, and ultimately the cloning of Lr34/Yr18, it became clear that RL6077 lacked the Lr34/Yr18a resistance haplotype present in RL6058 and therefore contained a different APR gene (Kolmer et al., 2008; Lagudah et al., 2009).

Studies on mapping populations from crosses involving RL6077 using *P. triticina* and *P. striiformis* isolates from multiple locations in Canada, Mexico and Australia, established co-segregation of the respective APRs on chromosome 4DL (long arm of chromosome 4D, on the D genome of breadwheat) (Herrera-Foessel et al., 2011; Hiebert et al., 2010). These APR genes at the resistance locus on 4DL have been designated Lr67/Yr46.

Example 2. Cloning of the Lr67 (Syn=Yr46=Sr55=Pm46) Gene

In addition to the wheat genotype RL6077, two other wheat genotypes, NP876 and Sujata have been postulated to carry Lr67. This was based on the presence of the leaf tip necrosis phenotype (Ltn), slow rusting to leaf rust infection and the simple sequence repeat (SSR) marker allele linked to Lr67 in RL6077 (Hererra et al., 2011). As part of the strategy towards identification of co-segregating markers and cloning of the Lr67 gene, the present inventors developed recombinant inbred (RI) families from crosses involving the adult plant leaf and stripe rust susceptible parent, Avocet. These RI families were derived from the crosses Avocet x RL6077, Avocet x Sujata and Avocet x NP876. An F2 family from the cross Thatcher x Thatcher+Lr67 (RL6077) was also made. These RI families were then used in genetic mapping studies and mutational experiments as follows.

Firstly, a mutagenised population of a derived line from Avocet x RL6077 fixed for the Lr67 gene was conducted using gamma irradiation with a dosage of 20 krad from a $^{60}$Co source. Secondly, chemical mutagenesis using on ethyl methanesulfonate (EMS) under standard mutagenesis conditions was used to generate a mutant population using the wheat genotype RL6077. M2 progeny lines were produced from the mutagenised populations and each tested for loss of the resistance phenotype. Field evaluation of the M2 mutant progeny was carried out to identify loss of leaf and stripe rust resistance resulting from inactivation of the Lr67 gene. Putative mutants were further tested at the M3 and M4 stage to select homozygous susceptible lines. Plants of five gamma irradiated lines (designated γ318, γ676, γ1183, γ1239 and γ1656) and two EMS lines (designated emsSu1 and emsSu2) were identified as susceptible mutants. They all showed loss of both the leaf rust and stripe rust resistance phenotypes as well as the leaf tip necrosis phenotype, suggesting that a single gene was responsible for the three phenotypes. The wheat genotype background of the EMS mutants facilitated stem rust and powdery mildew assessments, and each of the mutants exhibited susceptibility to both diseases in contrast to the resistance observed in their sibs and original parent.

In an effort to identify DNA sequences at or closely linked to the Lr67 locus, fifteen homozygous recombinant inbred lines (RILs) each from resistant (Lr67R) and susceptible (Lr67S) phenotypes were selected and subjected to extensive AFLP and SSR analysis. A genome complexity reduction library based on PstI endonuclease restricted genomic library from pooled DNA of the 15 resistant and homozygous lines were assessed for SNP based markers. A comparative genomics approach was also conducted using sequences from a wheat BAC clone containing the SSR closely linked to Lr67 (Hererra et al., 2011) as an anchor point to identify orthologous genes from the rice and Brachypodium genomes (FIG. 1). A colinear region between Brachypodium chromosome 1 and rice chromosome 3 was then used to develop DNA markers to amplify corresponding sequences from wheat and Aegilops tauschii, closely related to the D genome progenitor to wheat chromosome 4DL (FIG. 1).

The DNA markers generated from AFLP and SNPs from the genome complexity reduction libraries produced linked markers to Lr67, but none co-segregated with all the fifteen homozygous resistant and susceptible recombinant inbred lines. However, DNA fragments isolated from different parts of a chaperonin-encoding gene containing a Hsp70 (heat shock protein, see FIG. 1) domain isolated from the comparative genomics approach was completely linked to the fifteen susceptible recombinant inbred lines and absent in the fifteen resistant lines (FIG. 2). The extent of the Hsp70 chaperonin linkage was verified in 500 recombinant inbred lines and was confirmed to show complete association with the Lr67 locus. Genomic DNA blot analysis provided additional evidence that the gene encoding the Hsp70 chaperonin was deleted in the Lr67 resistant parental lines, RL6077, Sujata and NP876. Given that susceptible mutants which were loss-of-function had been isolated for Lr67, it was unlikely that the deleted Hsp70 chaperonin gene in the resistant plants was sufficient for the Lr67 resistance phenotype. Consequently a search of all predicted gene sequences in the close vicinity (within 21 kb) of Hsp70 was performed and three other genes were identified by comparative genomics. These were genes with protein domains annotated on the rice or Brachypodium genome maps as encoding a Sec14B cytosolic factor family protein, a monosaccharide transporter (MST—closely related to sugar transporters-SUT) and a protein interacting/binding protein (PIP).

The nucleotide sequences of the corresponding genes in several wheat varieties and Lr67 mutants were determined. Sequence analysis of the parental lines Thatcher (Lr67 susceptible), Avocet (Lr67 susceptible) and Thatcher+Lr67 (RL6077) showed no differences in the Sec14B gene whereas the MST and PIP genes revealed sequence polymorphisms. Two SNPs (C/G and T/G) found in the SUT gene were unique to Lr67 containing wheats (FIG. 4) while an insertion/deletion polymorphism in PIP was not diagnostic for Lr67. Co-segregation of the SNPs in the SUT gene and Lr67 adult plant rust was established in 520 recombinant inbred lines. To ensure that no additional gene sequences were missed or unknown rearrangements in the wheat chromosome 4DL region that harbours Lr67 relative to the corresponding syntenic regions of Brachypodium (chromosome 1) and rice (chromosome 3), the equivalent regions from Aegilops tauschii (D genome progenitor) were analysed. A sequence contig of 70 kb showed the presence of the Hsp70, SUT and PIP genes located within a 21 kb fragment with no other predicted genes in the contig. No recombinants were detected between these three genes when 1152 plants were analysed from an F2 progeny population from the Thatcher x Thatcher+Lr67 cross.

Analysis of the mutants that were inactivated for the Lr67 phenotype, revealed three of the gamma mutants were deleted for the SUT, PIP and some of the markers identified from comparative genomics in the Lr67 region (FIG. 3, deletions shown as the dashed lines). However four of the mutants (two EMS mutants and two from gamma irradiation, namely γ318 and γ1239) retained the Lr67 co-segregating SUT and PIP genes. Sequence analysis of the SUT gene in these mutants found single nucleotide changes and small deletions in only the SUT gene and not in PIP. Each of the mutational changes in the four mutants occurred in amino acids found in conserved regions of hexose sugar transporters (FIG. 4). An additional four mutants, obtained by sodium azide mutagenesis of RL6077, also showed single nucleotide changes that altered the amino acid composition of the SUT gene. On the basis of the co-segregation, and mutational analysis the inventors inferred that the SUT gene was sufficient to confer the Lr67 resistance phenotype.

When tested against the full range of rust and mildew diseases, the wheat EMS mutants all showed susceptibility to leaf rust, stripe rust, stem rust and powdery mildew. Thus inactivation of a single gene, SUT, has an effect on multiple diseases. The SUT gene was therefore identified conclusively as the Lr67 gene.

The Lr67 gene encodes a protein with 514 amino acids (FIG. 5) predicted to contain 12 transmembrane domains. When predicted using the TMHMM Server v2.0 and the PSIPRED v3.3 program, the transmembrane domains were predicted to be for amino acids: TMhelix1, 20-42; TMhelix2, 81-100; TMhelix3, 107-126; TMhelix4, 136-158; TMhelix5, 170-192; TMhelix6, 202-221; TMhelix7, 282-304; TMhelix8, 319-341; TMhelix9, 348-370; TMhelix10, 380-402; TMhelix11, 423-445; and TMhelix12, 450-472. Each of the following amino acid regions: the N-terminal 19 amino acids, the amino acids between TMhelices 2 and 3, the amino acids between TM helices 4 and 5, the amino acids between TM helices 6 and 7, the amino acids between TMA helices 8 and 9, and the C-terminal 42 amino acids were predicted by the same program to be located to the inside of the membrane, and the other amino acids outside of the membrane. The protein is a member of the Major Facilitator Superfamily (MFS) which is a large and diverse group of secondary transporters that include uniporters, symporters and antiporter proteins that facilitate transport across cytoplasmic or internal cell membranes of a variety of compounds including sugars. Homologous polypeptides were identified by querying the NCBI protein database with the amino acid sequence of SEQ ID NO:1, and numerous homologs identified. The amino acid sequence of Lr67 is about 89-93% identical to homologous polypeptides in several cereals including rice, and about 80% identical to a homolog in Arabidopsis, Sugar transport protein 13 (Accession No. NP_198006).

A DNA fragment corresponding to the Lr67 gene was cloned from wheat and its nucleotide sequences compared to the cDNA sequence (SEQ ID NO:10). This revealed the presence of two introns in the protein coding region of the gene (FIG. 14).

RT-PCR analysis showed that all three of the homoeologous Lr67 genes in the A, B and D genomes of hexaploid wheat were expressed in the plants. The polypeptide encoded by the A genome homoeolog of the Lr67 gene was 507/514 (98.6%) identical in amino acid sequence relative to SEQ ID NO:1, including having a glycine at position 144 and a valine at position 387 which were typical of the susceptible Lr67 polypeptides. This result indicated to the inventors that the resistant Lr67 polypeptide might act as a dominant-negative polypeptide, reducing the activity of the susceptible Lr67 polypeptides encoded by the A and B genomes in hexaploid wheat.

The molecular basis for the differences between the polypeptides encoded by the Lr67 resistant and susceptible alleles was delimited to the two nucleotide changes that gave rise to the SNPs used in the Lr67 diagnostic markers. These two nucleotide changes results in a change of amino acids from a conserved glycine to arginine (position 144) in the predicted fourth trans-membrane domain and a valine to leucine (position 387) in the tenth trans-membrane domain (FIGS. 6, 7 and 8) with reference to SEQ ID NO:1. These two nucleotide changes were rare in wheat and were not found in the D genome progenitor or in most commercial wheat cultivars with the exception of the few that carry Lr67. Therefore, Lr67 resistance may have originated subsequent to the formation of hexaploid wheat by hybridization from its diploid ancestral wheats. When over a 1000 wheat landraces and accessions from a wide range of geographical sources were analysed for the two Lr67 diagnostic markers, the mutation that gave rise to Lr67 was very rare and localized to a subset of landraces sourced from the Indo-Gangetic plains.

The homologs in other plant species such as Sugar transport protein 13 in Arabidopsis and in cereals, without exception, do not have arginine at the position corresponding to amino acid position 144 of SEQ ID NO: 1 or the leucine corresponding to amino acid position 387. Invariably, the homologs had a glycine at the position corresponding to amino acid 144 and almost always a valine at position 387 (see, for example, the alignments provided in FIGS. 9 and 10). These two amino acids were therefore highly conserved in the SUT polypeptides, and the mutation to either one, or both, amino acids indicative of an altered function that is the cause of the resistance phenotype to the rust and mildew pathogens.

Example 3. Glucose Uptake Studies on Lr67 (SUT) Expressed in Yeast-Variation in Polypeptide Sequence The demonstration that the Lr67 gene encoded a protein that showed homology to known sugar transporters led the inventors to test the function of the Lr67 polypeptides for sugar transport in yeast cells.
Experimental Procedure
The following experiments were completed using the protein coding regions for the Lr67 polypeptides (resistant and susceptible alleles) cloned into the yeast expression vector pRS416. This vector contained the constitutive ADH1 promoter and CYC1 terminator for expression of the inserted coding regions. The yeast strain employed was a hexose transport deficient variant of Saccharomyces cerevisiae named EBY.VW4000. Uptake was determined using radio labelled [$^{14}$C] glucose with incorporation radio-assayed by liquid scintillation counting.
Results
Glucose Uptake Over Time
Yeast cells transformed with the genetic constructs for expression of either the resistant (Lr67(res)) or susceptible (Lr67(sus)) alleles of Lr67 were incubated with 100 μM [$^{14}$C] glucose for 10 minutes. Glucose uptake was tested at 2 minute intervals. Yeast cells expressing the Lr67 susceptible allele were shown to be capable of transporting glucose at a higher rate than yeast cells expressing the Lr67 resistant allele or empty vector (FIG. 11). Indeed, the cells expressing the Lr67 resistant allele did not show detectable glucose transport activity above the control, although this assay was carried out for only 10 min and was not sensitive.
Lr67 (Sus) Glucose Uptake Kinetics
Concentration-dependent uptake of [14C] glucose by Lr67(sus) displayed classical Michaelis-Menten saturation kinetics. The Lineweaver-Burk equation was used to convert data for linear regression analysis. Lr67(sus) was shown to display a high affinity for glucose, having a $K_m$ of 73 μM and $V_{max}$ of 3.02 nmol min$^{-1}$ g FW$^{-1}$ for this substrate (FIG. 12).
Amino Acid Conversion Analysis
As described above, there were two SNP differences at the nucleotide sequence level between the susceptible and resistant alleles of Lr67. This created the two amino acid substitutions in the protein product which include a glycine to arginine substitution at position 144 (G144R) and valine to leucine substitution at position 387 (V387L). In order to test if these amino acid substitutions, singly or together, could affect glucose uptake rates of LR67, the amino acids at positions 144 and 387 in the Lr67 resistant allele were individually converted to the equivalent amino acid present in the Lr67 susceptible allele (i.e. R144G and L387V) by mutagenesis of the cloned gene.

Yeast cells transformed with either Lr67(sus), Lr67(res), Lr67(res) R144G and Lr67(res) L387V were incubated with 100 μM [$^{14}$C] glucose for 10 minutes. Yeast cells expressing Lr67 (res) R144G were shown to be capable of transporting glucose at a higher rate than yeast cells expressing the Lr67 (res) or the Lr67 (res) L387V (FIG. 13), but not to the full extent of Lr67(sus). This indicated that position 144 was the more important amino acid of the two substituted amino acids for rust resistance function and that the conversion of glycine to arginine (G144R) or vice versa (R144G) altered the glucose transport rate of Lr67 polypeptide. However, the addition of the second amino acid substitution (L387V) also made a contribution to the glucose transport rate.

Since the deletion mutations in the Avocet x RL6077 created by gamma irradiation that deleted the Lr67 gene resulted in a susceptible allele to rust and mildew infection, the inventors concluded that the Lr67 (resistant) polypeptide must have a positive function in wheat cells, certainly to be transport of a saccharide other than glucose, most likely to be transport of a hexose sugar. That is, conversion of the Lr67 susceptible allele in wheat plants such as Avocet to the resistance allele required the arginine at position 144 and was improved by the presence of the leucine at position 387.

Example 4. Production of Transgenic Plants

Experiments are carried out with the cloned genes and the amino acid variants to introduce the genetic constructs into transgenic wheat, transforming wheat plants of the cultivar Fielder using standard *Agrobacterium*-mediated techniques, and other plants such as cereals, to increase the resistance to fungal pathogens such as rust and mildew. Experiments are also carried out to modify the genes encoding the *Arabidopsis thaliana* and *Vitis vinifera* homologs of Lr67 to encode mutant polypeptides having the arginine at position 144 and the leucine at position 387, and to convert them into resistant polypeptides, in order to provide resistance genes for these plant species and other plants.

Materials and Methods

The gene encoding Lr67 was used to transform barley plants as follows. A genomic fragment of 7133 bp was isolated from the wheat genotype Thatcher+Lr67. The fragment contained the full length genomic sequence for the Lr67 gene and included 1318 bp of the native promoter region and 1512 bp of the native terminator sequence including the 3' untranslated region. The Lr67 fragment was inserted into the binary transformation vector pWBVec8. The Lr67 binary vector was transformed into the *A. tumefaciens* strain AGL-1 and used to produce stably transformed barley plants (cv. Golden Promise) as described in Tingay et al. (1997).

Results

Eight independent transgenic plants were identified which were transformed with the Lr67 transgene. All eight plants and wild-type control plants which had been subjected to the tissue culture steps involved in transformation but lacking the Lr67 transgene were infected with barley leaf rust, infecting plants of the T0 generation. One of the advanced Lr67 transgenic lines was further tested at the T1 stage. The leaf rust infections and subsequent culture were performed on seedlings and mature plants of transgenic barley grown in a humidity chamber using the *Puccinia hordei* pathotype 4653P+ (University of Sydney PBIC culture number 990492), which is avirulent on plants with resistance genes Rph3, 5, 7, 10, 11, 14, and 15 and virulent on lines with resistance genes Rph1, 2, 4, 6, 8, 9, 12, 13, and 19.

Rust sporulation was observed on leaves of the control plants but not on the positive Lr67 transgenic plants of the T0 generation. All of the Lr67 transgenic plants exhibited earlier leaf senescence compared with the control plants, similar to the leaf senescence phenotype described as leaf tip necrosis that is a characteristic feature of Lr67-mediated resistance in wheat. When the T1 generation of plants were tested, all of the plants containing Lr67 showed the leaf rust resistance phenotype when tested on seedlings, whereas all of the plants lacking the Lr67 gene showed leaf rust susceptibility. These results confirmed that the isolated Lr67 gene was functionally active and was sufficient to confer leaf rust resistance in barley. These experiments also extended the range of pathogen species for which Lr67 conferred resistance to include *P. hordeii* in addition to *Puccinia striiformis, P. triticina, P. graminis,* and *Blumeria vulgaris*.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2013903161 filed 21 Aug. 2013, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Bam et al. (2008) Proc S Afr Sug Technol Ass 81:508-512.
Barker et al. (1983) Plant Mol. Biol. 2: 235-350.
Bender and Pretorius (2000) Acta Phytopathol Entomol Hung 35:95-101.
Bevan et al. (1983) Nucl. Acid Res. 11: 369-385.
Borghi (2001) Italian wheat pool. In: Bonjean A P, Angus W J (eds) The world wheat book: A history of wheat breeding. Intercept, London, pp 289-309.
Caldwell (1968) Breeding for general and/or specific plant disease resistance. In: Finlay K W, Shepherd K W (eds) Proc 3rd Int Wheat Genet Symp, Australian Academy of Science, Canberra, Australia, pp 263-272.
Bossolini et al. (2006) Theor. Appl. Genet. 113:1049-1062.
Brueggeman et al. (2002) Proc. Natl. Acad. Sci. USA 99:9328-9333.
Cadwell and Joyce (1992) PCR Methods Appl. 2:28-33.
Capecchi (1980) Cell 22:479-488.
Cheng et al. (1996) Plant Cell Rep. 15:653-657.
Clapp (1993) Clin. Perinatol. 20:155-168.
Cloutier et al. (2007) Plant Mol Biol 65:93-106.
Coco et al. (2001) Nature Biotechnology 19:354-359.
Coco et al. (2002) Nature Biotechnology 20:1246-1250.
Collins et al. (1999) Plant Cell 11:1365-1376.
Comai et al. (2004) Plant J 37: 778-786.
Crameri et al. (1998) Nature 391:288-291.

Curiel et al. (1992) Hum. Gen. Ther. 3:147-154.
Dyck et al. (1966) Can. J. Genet. Cytol. 8: 665-671.
Dyck (1977) Can J Genet Cytol 19:711-716.
Dyck (1987) Genome 29:467-469.
Dyck and Kerber (1970) Can J Genet Cytol 12:175-180.
Dyck et al. (1994) Genome 37:556-559.
Eggert et al. (2005) Chembiochem 6:1062-1067.
Eglitis et al. (1988) Biotechniques 6:608-614.
Feuillet et al. (2003) Proc Natl Acad Sci 100:15253-15258.
Fujimura et al. (1985) Plant Tissue Cultural Letters 2:74.
Garfinkel et al. (1983) Cell 27: 143-153.
German and Kolmer (1992) Theor. Appl. Genet. 84: 97-105.
Graham et al. (1973) Virology 54:536-539.
Grant et al. (1995) Plant Cell Rep. 15:254-258.
Greve (1983) J. Mol. Appl. Genet. 1: 499-511.
Harayama (1998) Trends Biotechnol. 16:76-82.
Hayden et al. (2008) Mol. Breed 21:271-281.
Henikoff et al. (2004) Plant Physiol 135: 630-636.
Herrera-Foessel et al. (2011) Theor Appl Genet DOI 10.1007/s00122-010-1439.
Hiebert et al., (2010) Theor Appl Genet 121: 1083-1091.
Huang et al. (2003) Genetics 164:655-664.
Hiebert et al. Theor Appl Genet (in press).
Hinchee et al. (1988) Biotech. 6:915.
Jézéquel et al. (2008) Biotechniques 45:523-532.
Joshi (1987) Nucl. Acid Res. 15: 6643-6653.
Joshi et al. (2004) Crop Science 44:792-796.
Kerber and Aung (1999) Phytopathology 89:518-521.
Kolmer (1996) Annu Rev Phytopathol 34:435-455.
Kolmer et al. (2003) Plant Disease 87: 859-866.
Kolmer et al. (2008) Crop Sci 48:1841-1852.
Krattinger et al. (2009) Science 323:1360-1363.
Lagudah et al. (2009) Theor Appl Genet 119:889-898.
Langridge et al. (2001) Aust. J. Agric. Res. 52: 1043-1077.
Lemieux (2000) Current Genomics 1: 301-311.
Leung et al. (1989) Technique 1:11-15.
Liang et al. (2006) Phytopathology 96:784-789
Lillemo et al. (2008) Theor Appl Genet 116:1155-1166.
Lu et al. (1993) J. Exp. Med. 178: 2089-2096.
Manly et al. (2001) Mammalian Genome 12:930-9321.
Medberry et al. (1992) Plant Cell 4: 185-192.
Medberry et al. (1993) Plant J. 3: 619-626.
McIntosh (1992) Plant Path 41:523-527.
McIntosh (2009) History and status of the wheat rusts. In: McIntosh R (ed) Proc 2009 BGRI tech workshop, Cd Sonora, Obregon Mexico, pp 11-24.
Needleman and Wunsch (1970) J. Mol Biol. 45:443-453.
Ness et al. (2002) Nature Biotechnology 20:1251-1255.
Niedz et al. (1995) Plant Cell Reports 14: 403-406.
Ostermeier et al. (1999) Nature Biotechnology 17:1205-1209.
Ow et al. (1986) Science 234: 856-859.
Prasher et al. (1985) Biochem. Biophys. Res. Comm. 126: 1259-68.
Salomon et al. (1984) EMBO J. 3: 141-146.
Sieber et al. (2001) Nature Biotechnology 19:456-460.
Singh (1992a) Phytopathology 82:835-838.
Singh (1992b) Crop Science 32: 874-878.
Singh and Rajaram (1994) Euphytica 72: 1-7.
Slade and Knauf (2005) Transgenic Res. 14: 109-115.
Spielmeyer et al. (2005) Theor Appl Genet 111:731-735.
Spielmeyer et al. (2008) Theor Appl Genet 116:481-490.
Stalker et al. (1988) Science 242:419-423.
Stemmer (1994a) Proc. Natl. Acad. Sci. USA 91:10747-10751.
Stemmer (1994b) Nature 370(6488):389-391.
Thillet et al. (1988) J. Biol. Chem. 263:12500.
Tingay et al. (1997) Plant J. 11:1369-1376.
Toriyama et al. (1986) Theor. Appl. Genet. 205:34.
Volkov et al. (1999) Nucleic Acids Research 27:e18.
Wagner et al. (1992) Proc. Natl. Acad. Sci. USA 89:6099-6103.
Zhao et al. (1998) Nature Biotechnology 16:258-261.

The invention claimed is:

1. A genetically modified plant comprising a gene encoding an Lr67 polypeptide which comprises amino acids having a sequence at least 80% identical to the amino acid sequence of SEQ ID NO:1, wherein the gene has a genetic modification such that the polypeptide does not comprise a glycine at a position corresponding to amino acid number 144 of SEQ ID NO:1.

2. The genetically modified plant of claim 1, wherein when expressed in the plant, the Lr67 polypeptide confers upon the plant resistance to one or more biotrophic fungal pathogen(s).

3. The genetically modified plant of claim 2, wherein the one or more biotrophic fungal pathogen(s) is selected from the group consisting of *Blumeria graminis* f. sp. *tritici*, *Fusarium graminearum*, *Bipolaris sorokiniana*, *Erysiphe graminis* f. sp. *tritici*, *Puccinia graminis* f sp. *tritici*, *Puccinia striiformis*, *Puccinia hordei* and *Puccinia recondite* f. sp. *tritici*.

4. The genetically modified plant of claim 1, wherein the Lr67 polypeptide comprises an amino acid sequence which is at least 85% identical to the amino acid sequence of SEQ ID NO:1.

5. The genetically modified plant of claim 1 which has enhanced resistance to one or more biotrophic fugal pathogen(s) when compared to an isogenic plant lacking the genetic modification.

6. The genetically modified plant of claim 1 which has enhanced resistance to one or more biotrophic fungal pathogen(s) at the seedling stage of growth.

7. The genetically modified plant of claim 1 which is a cereal, grape, beet or leguminous plant.

8. A seed of the genetically modified plant of claim 1 which comprises the gene.

9. A method of producing a genetically modified plant, the method comprising the steps of
   i) genetically modifying a cell of a plant such that it comprises a gene encoding an Lr67 polypeptide which comprises amino acids having a sequence at least 80% identical to the amino acid sequence of SEQ ID NO:1, wherein the gene has a genetic modification such that the polypeptide does not comprise a glycine at a position corresponding to amino acid number 144 of SEQ ID NO:1, and
   ii) regenerating a transgenic plant from the cell, thereby producing the transgenic plant.

10. A method of producing a plant part, the method comprising,
    a) growing a plant of claim 1, and
    b) harvesting the plant part.

11. A method of producing flour, wholemeal, starch or other product obtained from seed, the method comprising:
    a) obtaining seed of claim 8, and
    b) extracting the flour, wholemeal, starch or other product.

12. A product produced from the plant of claim 1 or seed thereof, wherein the product is a food product or beverage product which comprises the gene.

13. An isolated and/or exogenous polynucleotide comprising nucleotides having a sequence as provided in SEQ ID NO:2 or SEQ ID NO:3, or a sequence which is at least 80% identical to one or both of SEQ ID NO:2 and SEQ ID NO:3, wherein the polynucleotide encodes an Lr67 polypeptide which does not comprise a glycine at a position corresponding to amino acid number 144 of SEQ ID NO:1, and wherein the polynucleotide is operably linked to a heterologous promoter.

14. A chimeric vector comprising the polynucleotide of claim 13.

15. A method of producing a genetically modified plant, the method comprising the steps of
    i) introducing a polynucleotide of claim 13 into a cell of a plant, and
    ii) regenerating a genetically modified plant from the cell, thereby producing the transgenic plant.

16. A method of selecting a genetically modified plant, the method comprising the steps of
    i) screening one or more progeny plants from the cross of two parental plants for the presence or absence of a polynucleotide of claim 13, wherein at least one plant comprises the polynucleotide, and
    ii) selecting a progeny plant which comprises the polynucleotide,
    thereby selecting the genetically modified plant.

* * * * *